US012708255B2

(12) United States Patent
Romo et al.

(10) Patent No.: US 12,708,255 B2
(45) Date of Patent: Aug. 18, 2026

(54) SYSTEMS AND METHODS FOR MODULAR ENDOSCOPE

(71) Applicant: Noah Medical Corporation, Redwood City, CA (US)

(72) Inventors: Enrique Romo, Danville, CA (US); Jian Zhang, San Mateo, CA (US); Carol Kayee Hung, Palo Alto, CA (US); Michael J. Shawver, Mill Valley, CA (US); Piotr Robert Slawinski, South San Francisco, CA (US); Kyle Ross Danna, Scotts Valley, CA (US); Hendrik Thompson, San Francisco, CA (US); Liya K. Abraha, San Francisco, CA (US)

(73) Assignee: Noah Medical Corporation, San Carlos, CA (US)

( * ) Notice: Subject to any disclaimer, the term of this patent is extended or adjusted under 35 U.S.C. 154(b) by 564 days.

(21) Appl. No.: 17/838,825

(22) Filed: Jun. 13, 2022

(65) Prior Publication Data

US 2022/0304550 A1 Sep. 29, 2022

Related U.S. Application Data

(63) Continuation of application No. PCT/US2020/066030, filed on Dec. 18, 2020.

(Continued)

(51) Int. Cl.

| | |
|---|---|
| ***A61B 1/005*** | (2006.01) |
| ***A61B 1/00*** | (2006.01) |
| ***A61B 1/06*** | (2006.01) |

(52) U.S. Cl.

CPC ........ *A61B 1/0057* (2013.01); *A61B 1/00096* (2013.01); *A61B 1/0055* (2013.01); *A61B 1/0676* (2013.01); *A61B 1/00117* (2013.01)

(58) Field of Classification Search

CPC ... A61B 1/0057; A61B 1/00147; A61B 1/005; A61B 1/0051; A61B 1/0055;

(Continued)

(56) References Cited

U.S. PATENT DOCUMENTS 6,251,092 B1 6/2001 Qin et al.
6,544,215 B1 4/2003 Bencini et al.

(Continued)

FOREIGN PATENT DOCUMENTS

CN 104720732 A 6/2015
CN 105939647 A 9/2016

(Continued)

OTHER PUBLICATIONS

EP20904108.6 Extended European Search Report dated Jan. 15, 2024.

(Continued)

*Primary Examiner* — Ryan N Henderson
*Assistant Examiner* — Pamela F Wu
(74) *Attorney, Agent, or Firm* — Wilson Sonsini Goodrich & Rosati

(57) ABSTRACT

An articulating flexible endoscope is provided. The endoscope comprises: a distal tip portion that is steerable via a driving mechanism; a bending section connected to the distal tip portion at a first end, and connected to a shaft portion at a transition interface, the bending section is articulated by one or more pull wires; and the shaft portion comprising one or more load transmission tubes for reducing at least a portion of the articulation force applied to the bending section by the one or more pull wires thereby improving stability of the shaft portion, the one or more load transmission tubes are anchored to the transition interface and have a length greater than the length of the shaft portion.

18 Claims, 18 Drawing Sheets

Related U.S. Application Data

(60) Provisional application No. 63/091,268, filed on Oct. 13, 2020, provisional application No. 62/950,740, filed on Dec. 19, 2019.

(58) Field of Classification Search
CPC ...... A61B 1/008; A61B 2034/301–306; A61B 1/00105; A61B 1/00071; A61B 1/012; A61M 25/0147
USPC ......................................... 600/104, 128, 139
See application file for complete search history.

(56) References Cited

U.S. PATENT DOCUMENTS 6,551,237 B2 4/2003 Matsui
6,551,271 B2 4/2003 Nguyen
7,591,783 B2 9/2009 Boulais et al.
7,811,277 B2 10/2010 Boulais
9,820,634 B2 11/2017 Simchony et al.
11,007,026 B2 5/2021 Kowshik
11,103,127 B2 8/2021 Sekowski et al.
2002/0165430 A1 11/2002 Matsui
2006/0025993 A1 2/2006 Aarts et al.
2006/0069310 A1* 3/2006 Couvillon, Jr. ........ A61B 1/009 600/152
2006/0074383 A1 4/2006 Boulais
2006/0200000 A1* 9/2006 Sato .................... A61B 1/0057 600/146
2006/0270975 A1 11/2006 Savage
2007/0233040 A1* 10/2007 Macnamara ......... A61B 1/0055 604/523
2008/0300462 A1 12/2008 Intoccia et al.
2009/0062606 A1* 3/2009 Ueda .................. A61B 1/00078 600/114
2009/0287047 A1 11/2009 Onoda et al.
2010/0113875 A1 5/2010 Yi et al.
2011/0015649 A1 1/2011 Anvari et al.
2011/0152880 A1 6/2011 Alvarez et al.
2011/0295065 A1* 12/2011 Gurusamy ........... A61B 1/0057 600/141
2015/0119637 A1 4/2015 Alvarez et al.
2016/0029878 A1 2/2016 Yamazaki et al.
2016/0184032 A1* 6/2016 Romo .................... B25J 13/085 901/46
2016/0316997 A1* 11/2016 Viebach ................ B60T 11/046
2016/0367119 A1 12/2016 OuYang et al.
2017/0119481 A1* 5/2017 Romo ................ A61B 1/00096
2018/0311473 A1 11/2018 Laby et al.
2018/0325499 A1 11/2018 Landey et al.
2019/0246873 A1 8/2019 Lu et al.
2019/0365209 A1 12/2019 Ye et al.

FOREIGN PATENT DOCUMENTS

EP 3087898 A1 11/2016
WO WO-2008018256 A1 2/2008
WO WO-2018220867 A1 12/2018
WO WO-2021127449 A1 6/2021

OTHER PUBLICATIONS

PCT/US2020/066030 International Search Report and Written Opinion dated Mar. 31, 2021.

* cited by examiner

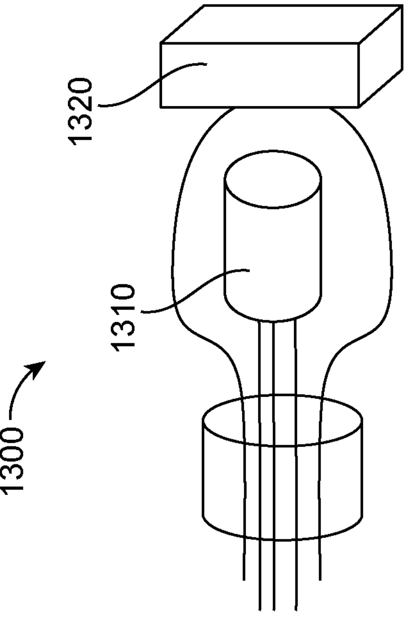
FIG. 13
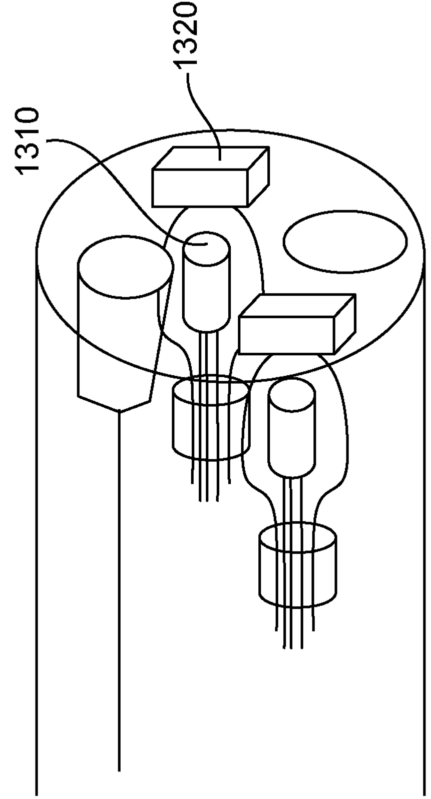

SYSTEMS AND METHODS FOR MODULAR ENDOSCOPE

REFERENCE

This application is a Continuation Application of International Application No. PCT/US2020/066030, filed Dec. 18, 2020, which claims priority to U.S. Provisional Patent Application No. 62/950,740, filed Dec. 19, 2019, and U.S. Provisional Patent Application No. 63/091,268, filed on Oct. 13, 2020, each of which is entirely incorporated herein by reference.

BACKGROUND OF THE INVENTION

Endoscopy procedures use an endoscope to examine the interior of a hollow organ or cavity of the body. Unlike many other medical imaging techniques, endoscopes are inserted into the organ directly. Flexible endoscope that can deliver instinctive steering and control is useful in diagnosing and treating diseases that are accessible through any natural orifice in the body. Depending on the clinical indication, the endoscope may be designated as bronchoscope, ureteroscope, colonoscope, gastroscope, ENT scope, and various others. For example, flexible endoscopy has been used to inspect and treat disorders of the gastrointestinal (GI) tract without the need for creating an opening on the patient's body. The endoscope is introduced via the mouth or anus into the upper or lower GI tracts respectively. A miniature camera at the distal end captures images of the GI wall that help the clinician in their diagnosis of the GI diseases. Simple surgical procedures (like polypectomy and biopsy) can be performed by introducing a flexible tool via a working channel to reach the site of interest at the distal end.

Endoscopes are traditionally made to be re-usable, which may require thorough cleaning, dis-infection, and/or sterilization after each procedure. In most cases, cleaning, disinfection, and sterilization may be aggressive processes to kill germs and/or bacteria. Such procedures may also be harsh on the endoscopes themselves. Therefore, the designs of such re-usable endoscopes can often be complicated, especially to ensure that the endoscopes can survive such harsh cleaning, dis-infection, and sterilization protocols. Periodical maintenance and repairs for such re-usable endoscopes may often be needed.

Low cost, disposable medical devices designated for a single-use have become popular for instruments that are difficult to clean properly. Single-use, disposable devices may be packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. Traditional endoscopes often include a handle that operators use to maneuver the endoscope. For single-use endoscopes, the handle usually encloses the camera, expensive electronics, and mechanical structures at proximal end in order to transmit the video and allow the users to maneuver the endoscope via a user interface. This may lead to high cost of the handle for a single-use endoscope.

SUMMARY OF THE INVENTION

Recognized herein is a need for an endoscope that allows for performing surgical procedures or diagnostic operations with improved performance and cost-efficiency. Recognized also herein are devices and systems comprising endoscopes which may be disposable and may not require extensive cleaning procedures. The present disclosure provides low-cost, single-use articulatable endoscope for diagnosis and treatment in various applications such as bronchoscopy, urology, gynecology, arthroscopy, orthopedics, ENT, gastro-intestine endoscopy, neurosurgery, and various others. It should be noted that the provided endoscope systems can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others It should be noted that the provided modular endoscope components and various components of the device can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

In an aspect, an articulating flexible endoscope is provided. The articulating flexible endoscope comprises: a distal tip portion that is steerable via a driving mechanism; a bending section connected to the distal tip portion at a first end, and connected to a shaft portion at a transition interface, wherein the bending section is articulated by one or more pull wires; and the shaft portion comprising one or more load transmission tubes for accommodating the one or more pull wires thereby improving stability of the shaft portion.

In some embodiments, the distal tip portion comprises a structure to receive an imaging device, a position sensor, and an illumination device. In some embodiments, each of the one or more pull wires is placed inside of a lumen of a respective load transmission tube from the one or more load transmission tubes. In some embodiments, the bending section is bent by the one or more pull wires in two or more directions. In some embodiments, the one or more load transmission tubes are anchored to the transition interface and have a length greater than the length of the shaft portion. In some embodiments, the one or more load transmission tubes have a non-linear configuration. In some embodiments, the one or more load transmission tubes have a spiral configuration.

In some embodiments, the shaft portion includes a tube with an integrally formed structure to vary a stiffness of the shaft portion. In some embodiments, the articulating flexible endoscope further comprises a deformable working channel. In some embodiments, the articulating flexible endoscope further comprises a handle portion, wherein the handle portion includes one or more components configured to process image data, provide power to one or more electronic components located at the distal tip portion, or establish communication with an external device. In some cases, the handle portion comprises an interface configured to couple the handle portion to an instrument driving mechanism. In some instances, the interface is an electrical interface and a mechanical interface. In some cases, the handle portion comprises a mechanical control module for interfacing an irrigation system or aspiration system.

In another aspect, a disposable endoscope is provided. The disposable endoscope comprises: a distal tip portion including an imaging device, a position sensor and an illumination device; a bending section connected to the distal tip portion at a first end, and connected to a shaft portion at a second end, wherein the bending section is articulated by one or more pull wires; and the shaft portion comprising one or more load transmission tubes for accommodating the one or more pull wires thereby improving stability of the shaft portion.

In some embodiments, the distal tip portion comprises a structure to receive the imaging device, the position sensor, and the illumination device. In some embodiments, the imaging device, the position sensor, and the illumination device are arranged into a compact configuration. In some embodiments, the one or more load transmission tubes have a length greater than the length of the shaft portion.

In some embodiments, each of the one or more pull wires is placed inside of a lumen of a respective load transmission tube from the one or more load transmission tubes. In some embodiments, the one or more pull wires are movable relative to the one or more load transmission tubes. In some embodiments, the bending section is bent by the one or more pull wires in two or more directions. In some embodiments, the one or more load transmission tubes have a non-linear configuration. In some embodiments, the one or more load transmission tubes have a spiral configuration.

In some embodiments, the shaft portion includes a tube with an integrally formed structure to vary a stiffness of the shaft portion. In some embodiments, the disposable endoscope further comprises a deformable working channel. In some embodiments, the disposable endoscope further comprises a handle portion, wherein the handle portion includes one or more components configured to process image data, provide power to the imaging device, the position sensor and the illumination device, or establish communication with an external device. In some cases, the handle portion comprises an interface configured to couple the handle portion to an instrument driving mechanism. In some instances, the interface includes an electrical interface and a mechanical interface. In some examples, the mechanical interface is configured to releasably couple the handle portion to the instrument driving mechanism.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 13 shows an example of a compact configuration of a plurality of electronic elements disposed at a distal portion of a catheter, in accordance with some embodiments of the invention.

DETAILED DESCRIPTION OF THE INVENTION

Figure 1:
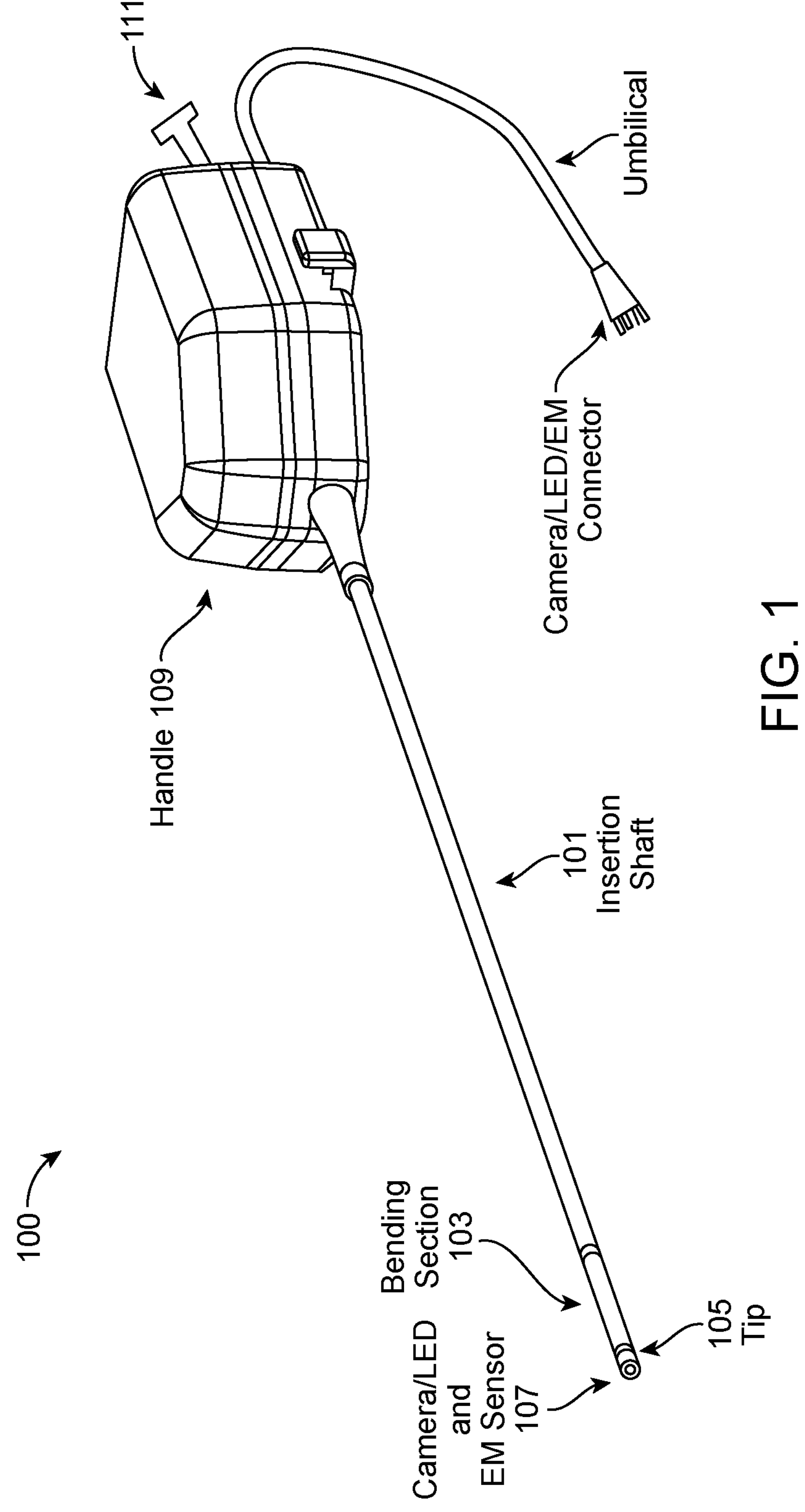
FIG. 1 illustrates an example of a flexible endoscope, in accordance with some embodiments of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

While exemplary embodiments will be primarily directed at a device or system for bronchoscopy, one of skill in the art will appreciate that this is not intended to be limiting, and the devices described herein may be used for other therapeutic or diagnostic procedures and in various anatomical regions of a patient's body. The provided device or system can be utilized in urology, gynecology, rhinology, otology, laryngoscopy, gastroenterology with the endoscopes, combined devices including endoscope and instruments, endoscopes with localization functions, one of skill in the art will appreciate that this is not intended to be limiting, and the devices described herein may be used for other therapeutic or diagnostic procedures and in other anatomical regions of a patient's body, such as such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat, and various others, in the forms of: NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, Orthopedic Endoscopes, and others, in combination with various tools or instruments.

The systems and apparatuses herein can be combined in one or more of many ways to provide improved diagnosis and therapy to a patient. Systems and apparatuses provided herein can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms distal and proximal may generally refer to locations referenced from the apparatus, and can be opposite of anatomical references. For example, a distal location of a primary shaft or catheter may correspond to a proximal location of an elongate member of the patient, and a proximal location of the primary sheath or catheter may correspond to a distal location of the elongate member of the patient.

Modular Flexible Endoscope

In an aspect of the invention, a flexible endoscope with improved performance at reduced cost is provided. FIG. 1 illustrates an example of a flexible endoscope 100, in accordance with some embodiments of the present disclosure. As shown in FIG. 1, the flexible endoscope 100 may comprise a handle portion 109 and a flexible elongate member to be inserted inside of a subject. In some embodiments, the flexible elongate member may comprise a shaft (e.g., insertion shaft 101), steerable tip (e.g., tip 105) and a steerable section (bending section 103). The endoscope 100 may also be referred to as steerable catheter assembly as described elsewhere herein. In some cases, the endoscope 100 may be a single-use robotic endoscope. In some cases, the entire catheter assembly may be disposable. In some cases, at least a portion of the catheter assembly may be disposable. In some cases, the entire endoscope may be released from an instrument driving mechanism and can be disposed of In some embodiment, the endoscope may contain varying levels of stiffness along the shaft, as to improve functional operation.

The endoscope or steerable catheter assembly 100 may comprise a handle portion 109 that may include one or more components configured to process image data, provide power, or establish communication with other external devices. For instance, the handle portion may include a circuitry and communication elements that enables electrical communication between the steerable catheter assembly 100 and an instrument driving mechanism (not shown), and any other external system or devices. In another example, the handle portion 109 may comprise circuitry elements such as power sources for powering the electronics (e.g. camera, electromagnetic sensor and LED lights) of the endoscope.

The one or more components located at the handle may be optimized such that expensive and complicated components may be allocated to the robotic support system, a hand-held controller or an instrument driving mechanism thereby reducing the cost and simplifying the design the disposable endoscope. In some cases, the handle portion may be in electrical communication with the instrument driving mechanism (e.g., FIG. 8, instrument driving mechanism 820) via an electrical interface (e.g., printed circuit board) so that image/video data and/or sensor data can be received by the communication module of the instrument driving mechanism and may be transmitted to other external devices/systems. In some cases, the electrical interface may establish electrical communication without cables or wires. For example, the interface may comprise pins soldered onto an electronics board such as a printed circuit board (PCB). For instance, receptacle connector (e.g., the female connector) is provided on the instrument driving mechanism as the mating interface. This may beneficially allow the endoscope to be quickly plugged into the instrument driving mechanism or robotic support without utilizing extra cables. Such type of electrical interface may also serve as a mechanical interface such that when the handle portion is plugged into the instrument driving mechanism, both mechanical and electrical coupling is established. Alternatively or in addition to, the instrument driving mechanism may provide a mechanical interface only. The handle portion may be in electrical communication with a modular wireless communication device or any other user device (e.g., portable/hand-held device or controller) for transmitting sensor data and/or receiving control signals.

In some cases, the handle portion 109 may comprise one or more mechanical control modules such as lure 111 for interfacing the irrigation system/aspiration system. In some cases, the handle portion may include lever/knob for articulation control. Alternatively, the articulation control may be located at a separate controller attached to the handle portion via the instrument driving mechanism.

The endoscope may be attached to a robotic support system or a hand-held controller via the instrument driving mechanism. The instrument driving mechanism may be provided by any suitable controller device (e.g., hand-held controller) that may or may not include a robotic system. The instrument driving mechanism may provide mechanical and electrical interface to the steerable catheter assembly 100. The mechanical interface may allow the steerable catheter assembly 100 to be releasably coupled to the instrument driving mechanism. For instance, a handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool. Details about the instrument driving mechanism are described later herein.

In the illustrated example, the distal tip of the catheter or endoscope shaft is configured to be articulated/bent in two or more degrees of freedom to provide a desired camera view or control the direction of the endoscope. As illustrated in the example, imaging device (e.g., camera), position sensors (e.g., electromagnetic sensor) 107 is located at the tip of the catheter or endoscope shaft 105. For example, line of sight of the camera may be controlled by controlling the articulation of the bending section 103. In some instances, the angle of the camera may be adjustable such that the line of sight can be adjusted without or in addition to articulating the distal tip of the catheter or endoscope shaft. For example, the camera may be oriented at an angle (e.g., tilt) with respect to the axial direction of the tip of the endoscope with aid of an optimal component.

The distal tip 105 may be a rigid component that allow for positioning sensors such as electromagnetic (EM) sensors, imaging devices (e.g., camera) and other electronic components (e.g., LED light source) being embedded at the distal tip.

In real-time EM tracking, the EM sensor comprising of one or more sensor coils embedded in one or more locations and orientations in the medical instrument (e.g., tip of the endoscopic tool) measures the variation in the EM field created by one or more static EM field generators positioned at a location close to a patient. The location information detected by the EM sensors is stored as EM data. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. For example, the EM field generator may be positioned close to the patient torso during procedure to locate the EM sensor position in 3D space or may locate the EM sensor position and orientation in 5D or 6D space. This may provide a visual guide to an operator when driving the bronchoscope towards the target site. Details about the tip design and the plurality of components embedded at the tip are described later herein.

The endoscope may have a unique design in the shaft component. In some cases, the insertion shaft of the endoscope may consist of a single tube that incorporates a series of cuts (e.g., reliefs, slits, etc.) along its length to allow for improved flexibility as well as a desirable stiffness. Details about the shaft design is described later herein.

The bending section 103 may be designed to allow for bending in two or more degrees of freedom (e.g., articulation). A greater bending degree such as 180 and 270 degrees (or other articulation parameters for clinical indications) can be achieved by the unique structure of the bending section. In some cases, the bending section may be fabricated separately as a modular component and assembled to the insertion shaft. In some cases, the bending section may further incorporate minimalist features thereby reducing cost and increasing reliability. For example, the bending section may incorporate a cut pattern that beneficially allows for a greater degree of tube deflection to achieve a desired tip displacement relative to the insertion shaft.

Figure 2:
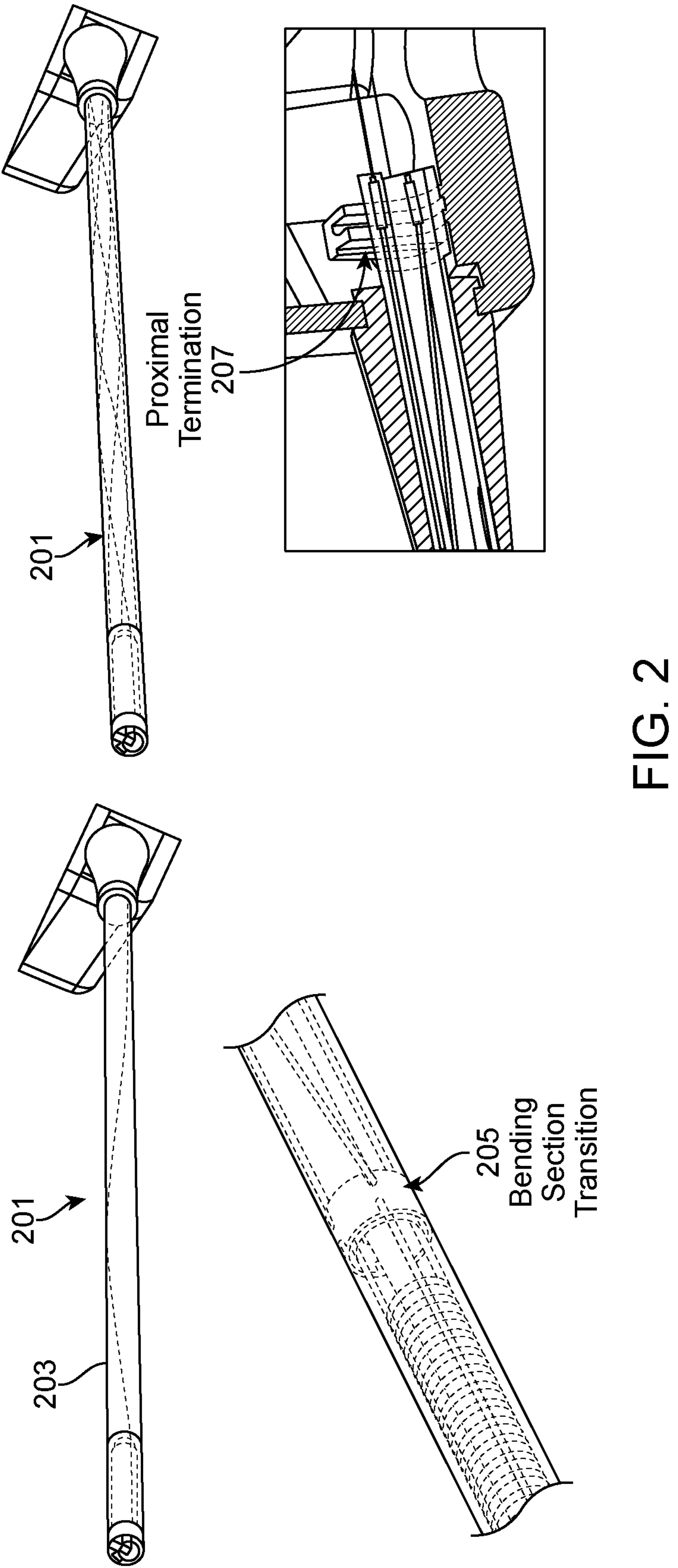
FIG. 2 shows an example of an endoscope with an articulation force transmission mechanism, in accordance with some embodiments of the invention.

In some embodiments, the bending section or the endoscope may comprise an articulation force transmission mechanics to ensure that the endoscope is stable and delivers instinctive bending section responsiveness. FIG. 2 shows an example of an endoscope with an articulation force transmission mechanism 201, in accordance with some embodiments of the invention. The articulation force transmission mechanism 201 may include a plurality of load transmission tubes that are located inside the bore of the insertion shaft/tube. In some cases, at least one, two, three, four, five or more load transmission tubes may be included to reduce the axial compression/extension (strain) of the insertion tube 203 during articulation of the bending section. The load transmission tubes may transmit at least a portion of the articulation load applied to the bending section and/or the shaft back to the handle (e.g., via actuator or motors that drive one or more articulating pull wires).

The shaft portion may comprise one or more load transmission tubes for accommodating the one or more pull wires. The transmission tubes counteract the articulation loads allowing for an improved stability of the insertion shaft. The plurality of load transmission tubes 201 may reside within the lumen of the shaft tube (i.e., tube bore) and be configured to transfer articulation reaction forces from the bending section to the handle portion. The load transmission tubes are configured to transfer the bending section articulation reaction forces back to the handle portion thereby reducing the articulation forces that would have been applied to the insertion shaft tube. Such design may beneficially prevent these articulation forces from being resolved through the insertion shaft tube thus providing a stable shaft. The transmission modality described herein may ensure that the insertion shaft tube experiences minimal axial compressive or extension forces, thereby remaining stable during the articulation of the bending section.

In preferred embodiments of the load transmission mechanism, the plurality of load transmission tubes 201 may be longer than the length of the insertion shaft tube 203. The length of the plurality of load transmission tubes 201 may be determined such that when the load transmission tubes are under axial compression, they are still longer than the length of the insertion shaft tube 203 thereby preventing loads from transferring through the insertion shaft tube. For example, the length of the load transmission tubes may be at least 0.01%, 0.1%, 0.2%, 0.3%, 1%, 5%, 10% longer than the length of the insertion shaft. The length of the load transmission tubes may be determined based at least in part on the dimension of the inner diameter of the shaft. For example, the load transmission tubes may have a spiral configuration that provides sufficient stiffness to bear/transmit the load.

The load transmission tubes may have a dimension and configuration that can accommodate a displacement within the shaft tube. For example, when the insertion shaft tube 203 is bent such as due to being subjected to a tortuous anatomy, the insertion shaft tube may cause displacement of components housed within the bore of the insertion shaft tube. In this case, the extra length of the load transmission tubes may beneficially accommodate the displacement within the insertion shaft tube bore while improving stability of the shaft. Compared to existing techniques that may utilize coil pipes and service loop within the handle portion, the modular design and assembly of the load transmission tubes may beneficially reduce the cost without comprising the performance of the shaft. Compared to other existing techniques that has the pull wires built into the shaft (shown in FIG. 6), the provided load transmission mechanism may beneficially transmit load from the bending section to the handle without compressing the shaft thereby improving the shaft stability.

The plurality of load transmission tubes may be anchored at the proximal end 207 and distal end 205 of the insertion shaft tube 203. As described above, because the load transmission tubes are longer than the length of the insertion shaft tube, the load transmission tubes may have a non-linear/straight configuration within the bore of the insertion shaft tube allowing for the flexibility to adjust to the displacement caused by bending. For example, the one or more load transmission tubes may have a non-straight (e.g., spiraled) configuration allowing for movement within the main lumen of the endoscope to account for geometry changes to the length of the shaft when the endoscope is subjected to tortuous configurations while being placed in the anatomy. Such load transmission mechanism may beneficially serve as a natural spring to counteract to the motion from the outer insertion shaft.

In some embodiments, the one or more load transmission tubes may enclose one or more pull wires. The articulation of the endoscope may be controlled by applying force to the distal end of the endoscope via one or multiple pull wires. The one or more pull wires may be attached to the distal end of the endoscope. In the case of multiple pull wires, pulling one wire at a time may change the orientation of the distal tip to pitch up, down, left, right or any direction needed. In some cases, the pull wires may be anchored at the distal tip of the endoscope, running through the bending section, and entering the handle where they are coupled to a driving component (e.g., pulley). This handle pulley may interact with an output shaft from the robotic system.

Figure 3A:
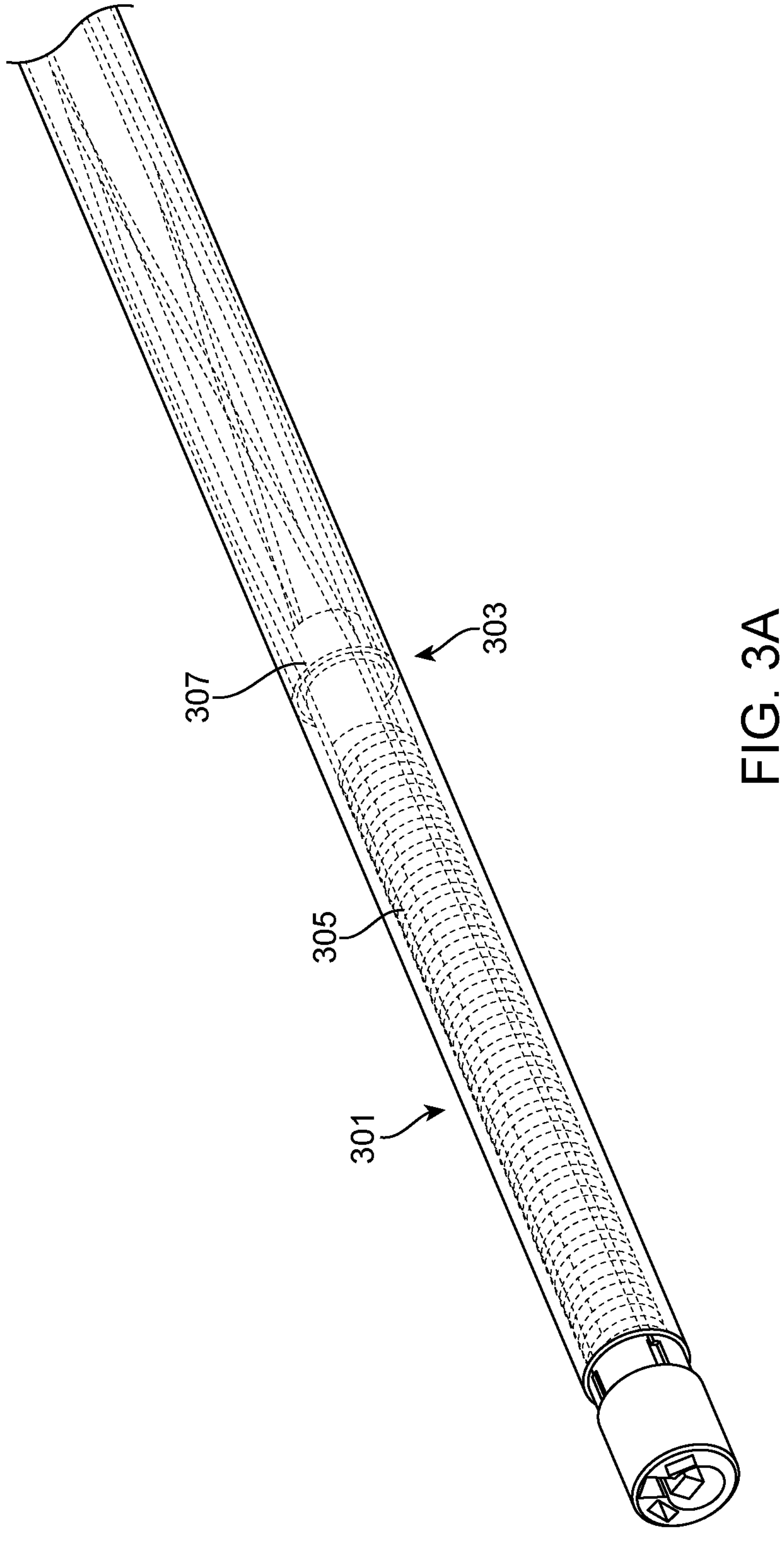
FIG. 3A and FIG. 3B show examples of one or more pull wires assembled with one or more load transmission tubes at a bending section.
Figure 3B:
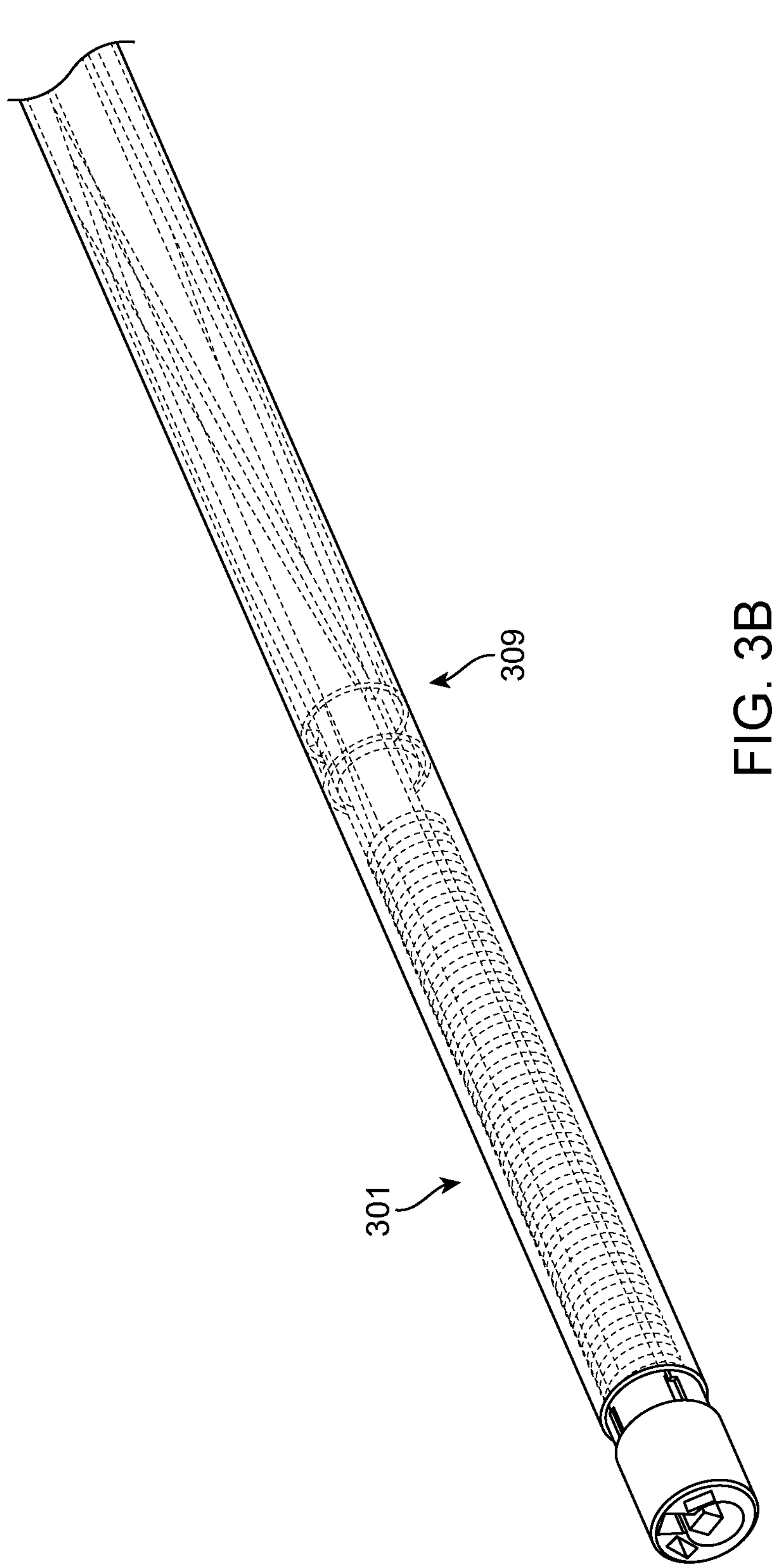

In some embodiments, the one or more pull wires may be located within the one or more load transmission tubes or running through the inside of the transmission tubes. FIG. 3A and FIG. 3B show examples of one or more pull wires 305 assembled with the load transmission tubes 307 at the bending section 301. As shown in FIG. 3A, the bending section 301 may be composed of stainless steel ribbon. The bending section may be formed of other suitable structures or materials to achieve pre-determined bending stiffness while maintaining desired axial and torsional stiffness with low articulation force. For example, the bending section may comprise braid structures for torsional stability. In the illustrated example, a plurality of pull wires 305 may run through or be placed inside of the lumen of the load transmission tubes 307 and the bending section, terminated at the tip of the endoscope.

For example, a driving mechanism (e.g., actuators, motors) may be engaged with the pull wires to articulate the bending section. The one or more load transmission tubes may be configured to transmit at least a portion of the articulation loads (e.g., compression) from the bending section back to the handle or motors, for example, by placing the one or more pull wires inside the one or more load transmission tubes, respectively. There may be relative motion between the pull wire and the corresponding load transmission tube during articulation. The one or more load transmission tubes may transmit at least a portion of the articulation load applied to the bending section and/or the shaft back to the handle (e.g., motors that drive one or more articulating pull wires). This may beneficially reduce at least a portion of the articulation force applied to the bending section and/or the insertion shaft thereby improving stability of the insertion shaft.

The endoscope may comprise a bending section transition 303 that is located at the junction interface of the bending section and the shaft. The bending section transition 303 may comprise structures that may enable efficient and convenient assembly of the endoscope. For example, the bending section transition 303 may include mechanical components such as snaps/clips to anchor the load transmission tubes (e.g., hypotubes) to the cutout features on the insertion shaft. FIG. 3B shows another example of the bending section transition 309. In the illustrated example, the load transmission tubes may be anchored to the interface between the insertion shaft and the bending section by welding to the transition ring structure of the bending section transition 309. This may beneficially reduce the abrupt stiffness change between the shaft portion and the bending section thereby preventing kinking.

Figure 4:
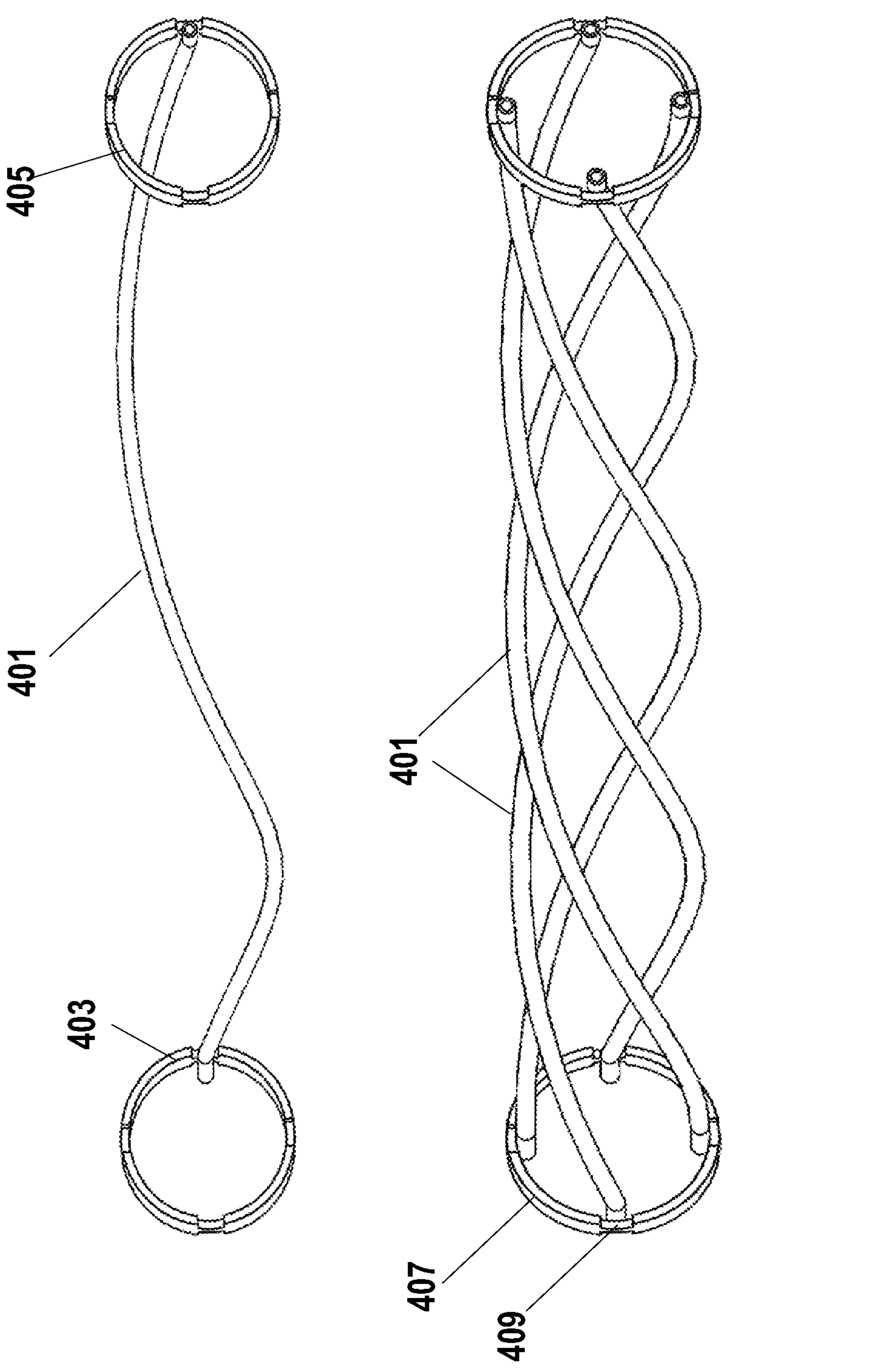
FIG. 4 shows an example of a load transmission tube terminated at a distal shaft region and proximal shaft region.

FIG. 4 shows an example of a load transmission tube 401 terminated at a distal shaft region 403 and proximal shaft region 405. As described above, the load transmission tube may have a non-linear/non-straight configuration within the bore of the insertion tube thereby allowing for the flexibility to adjust to the displacement caused by bending. The load transmission mechanism may comprise one or more load transmission tubes as shown in the example. Such load transmission mechanism may beneficially serve as a natural spring to counteract to the motion from the outer insertion shaft without requiring extra service loop at the handle portion. In the illustrated example, the end portion of the load transmission tube may be fixedly connected (e.g., welded to) the bending section transition 407. The bending section transition 407 may comprise a coupling structures 409 (e.g., snap) for easy assembling to the insertion shaft.

In some cases, the one or more load transmission tubes may be composed of materials such as metallic tubing or metallic wound coil pipe. The geometry and/or materials of the load transmission tubes may be selected/determined to provide desired axial and bending stiffness. For example, the material may be metallic materials such as stainless steel or nitinol, stiff polymers such as PEEK, glass or carbon filled PEEK, Ultem, Polysulfone and other suitable materials. In some cases, the one or more load transmission tubes may have an inner diameter greater than the outer diameter of the pull wire to allow for relative movement (e.g., translational and/or rotational movement) between the load transmission tubes and the pull wire. The wall thickness of the one or more load transmission tubes may be determined based on a function of the load transmission needed to transfer the articulation loads of the bending section.

Figure 5:
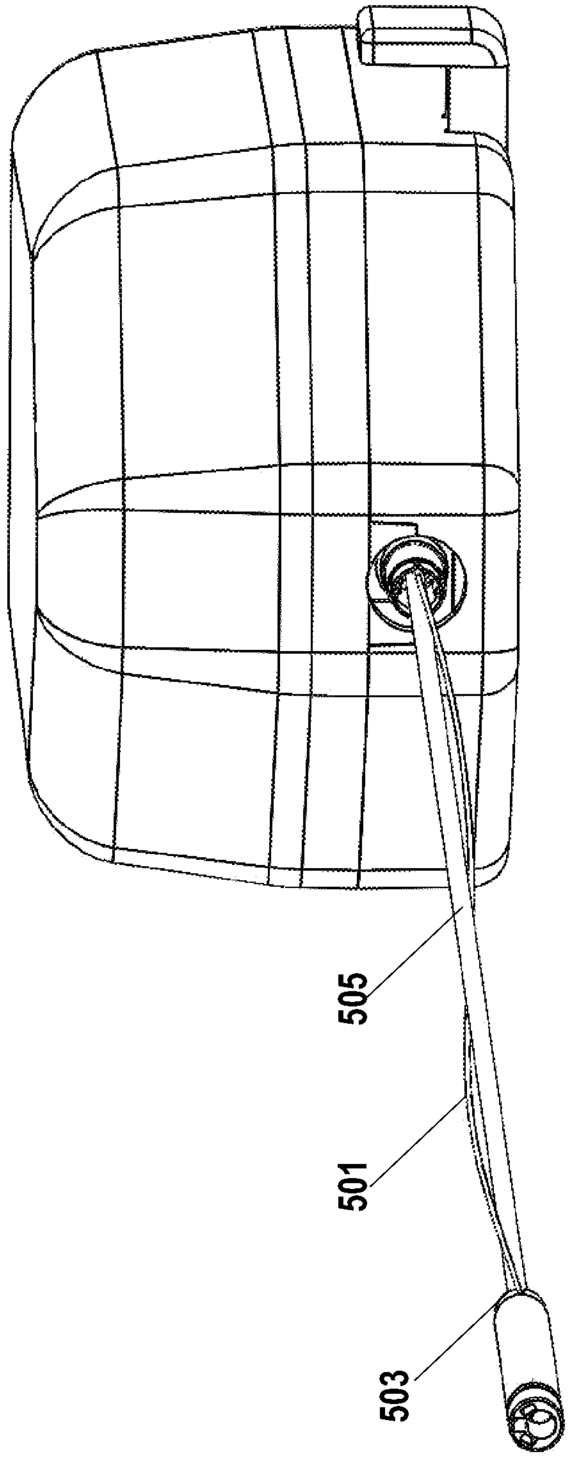
FIG. 5 shows an example of a load transmission tube terminated at a distal shaft region and proximal shaft region.

FIG. 5 shows an example of a load transmission tube 501 terminated at a distal shaft region 503 and proximal shaft region. As described elsewhere herein, the load transmission tube 501 may be located within the lumen of the insertion shaft (not shown) and external to the working channel 505.

Figure 6:
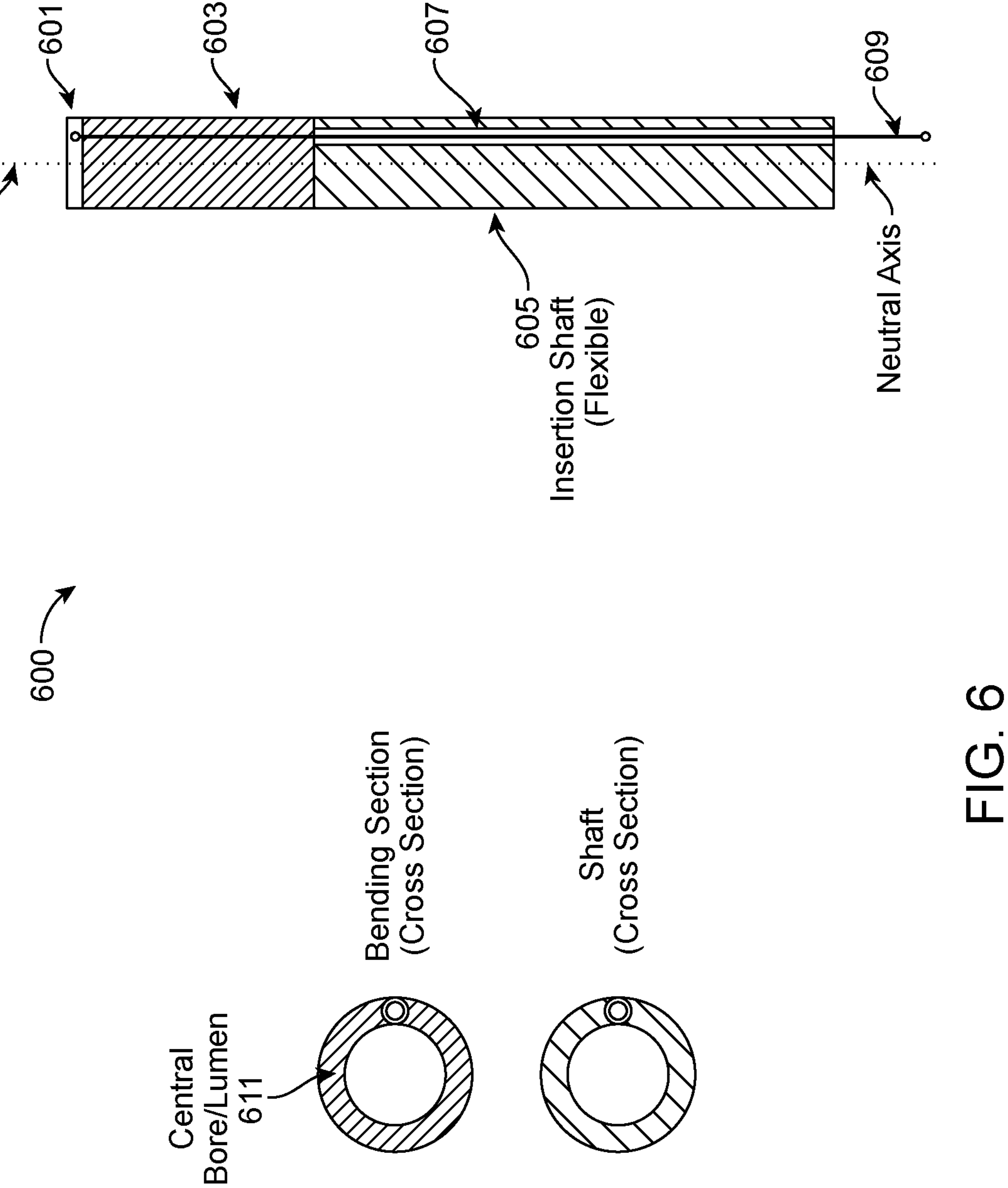
FIG. 6 shows an example of an existing steerable catheter architecture.

FIG. 6 shows an example of an existing steerable catheter architecture 600. In the existing catheter design, without load transmission tubes, the one or more pull wires 609 are usually running through conduits 607 that are built into the walls of the insertion shaft 605 and bending section 603. The catheter shaft may have a central bore/lumen 611 coaxial with the neutral axis. As shown in the cross-section view, the shaft wall or the bending section wall may have a built-in structure (e.g., lumens, conduits) to let the pull wires pass through. In such case, the shaft may bear the articulation load which may result in an unstable shaft.

Figure 7:
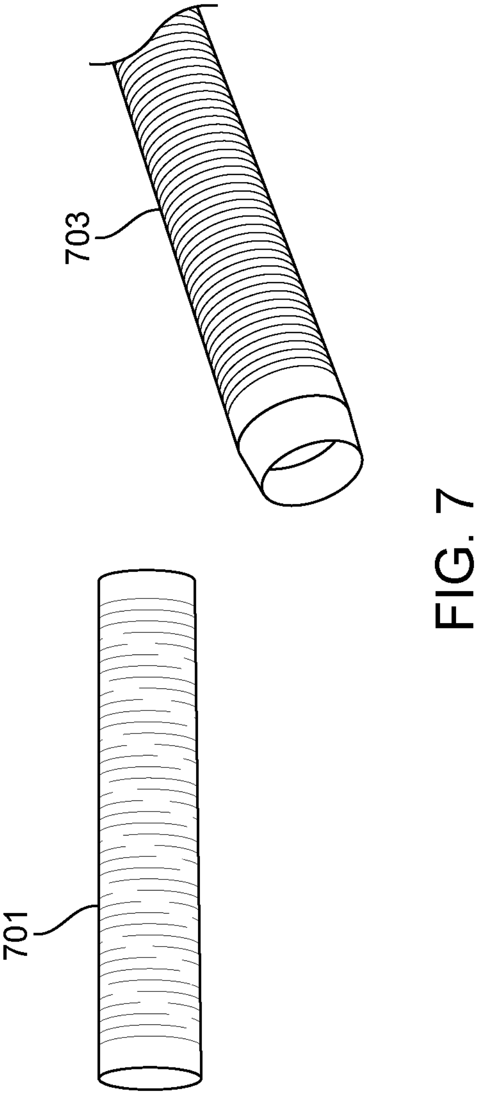
FIG. 7 shows an example of a design for an insertion shaft.

FIG. 7 shows examples of the design for the insertion shaft. As described above, the insertion shaft of the endoscope may consist of a single tube with an integrally formed structure to vary a stiffness of the shaft portion. For example, the tube may have a series of cuts (or reliefs, slits, etc.) formed along the length. The cuts in the tube may have varied profile/pattern 701, 703 and density along the length to generate a variable bending stiffness from the distal region to the proximal region. This may beneficially allow for controlling the bending stiffness parameters by controlling the cuts in the insertion shaft.

Low Cost and Single Use Robotic Bronchoscope

In another aspect of the invention, a single-use robotic bronchoscope is provided. The robotic bronchoscope can be the same as the steerable catheter assembly as described elsewhere herein. Traditional endoscopes can be complex in design and are usually designed to be re-used after procedures, which require thorough cleaning, dis-infection, or sterilization after each procedure. The existing endoscopes are often designed with complex structures to ensure the endoscopes can endure the cleaning, dis-infection, and sterilization processes. The provided robotic bronchoscope can be a single-use endoscope that may beneficially reduce cross-contamination between patients and infections. In some cases, the robotic bronchoscope may be delivered to the medical practitioner in a pre-sterilized package and are intended to be disposed of after a single-use.

Figure 8:
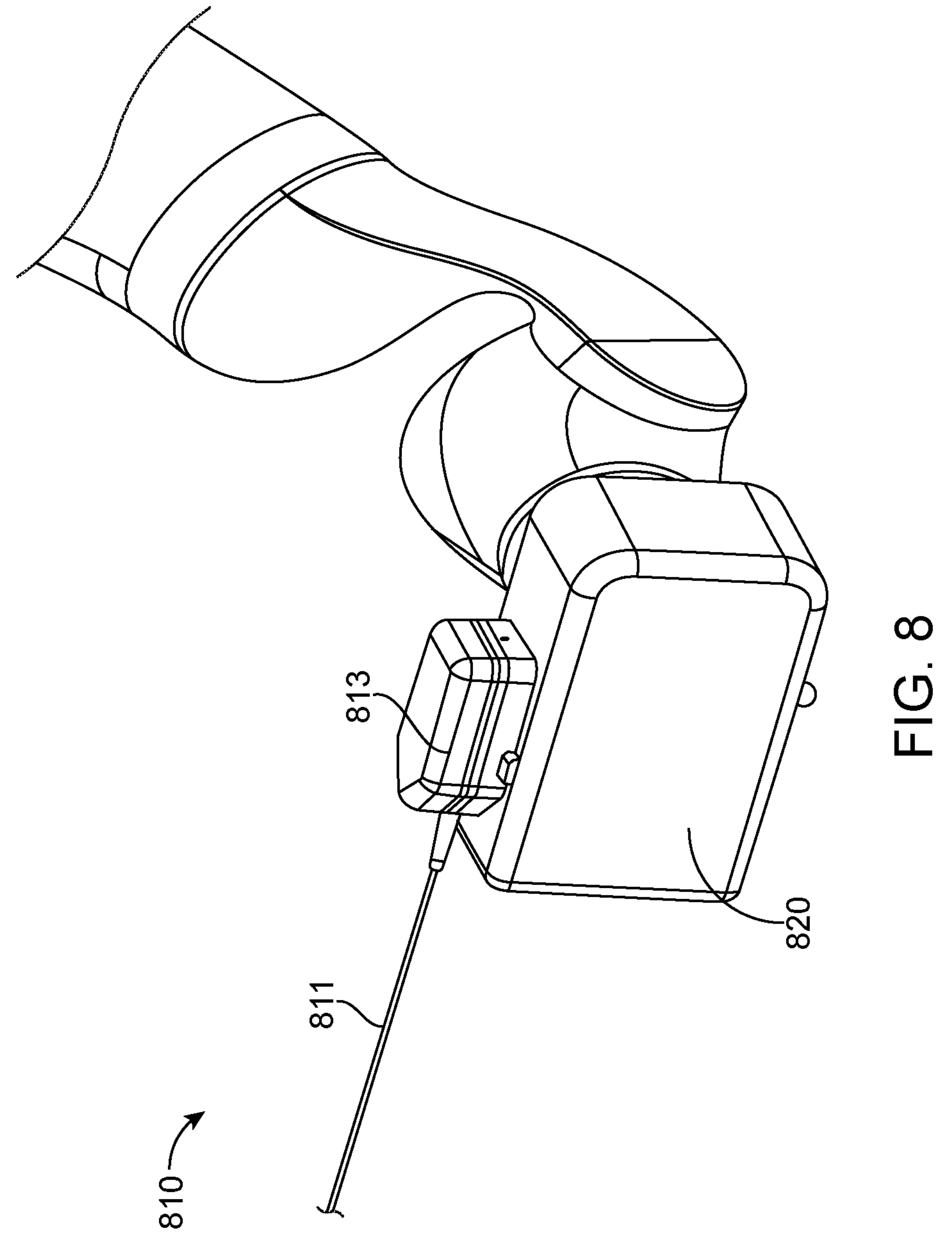
FIG. 8 shows an example of a robotic bronchoscope, in accordance with some embodiments of the invention.
Figure 9:
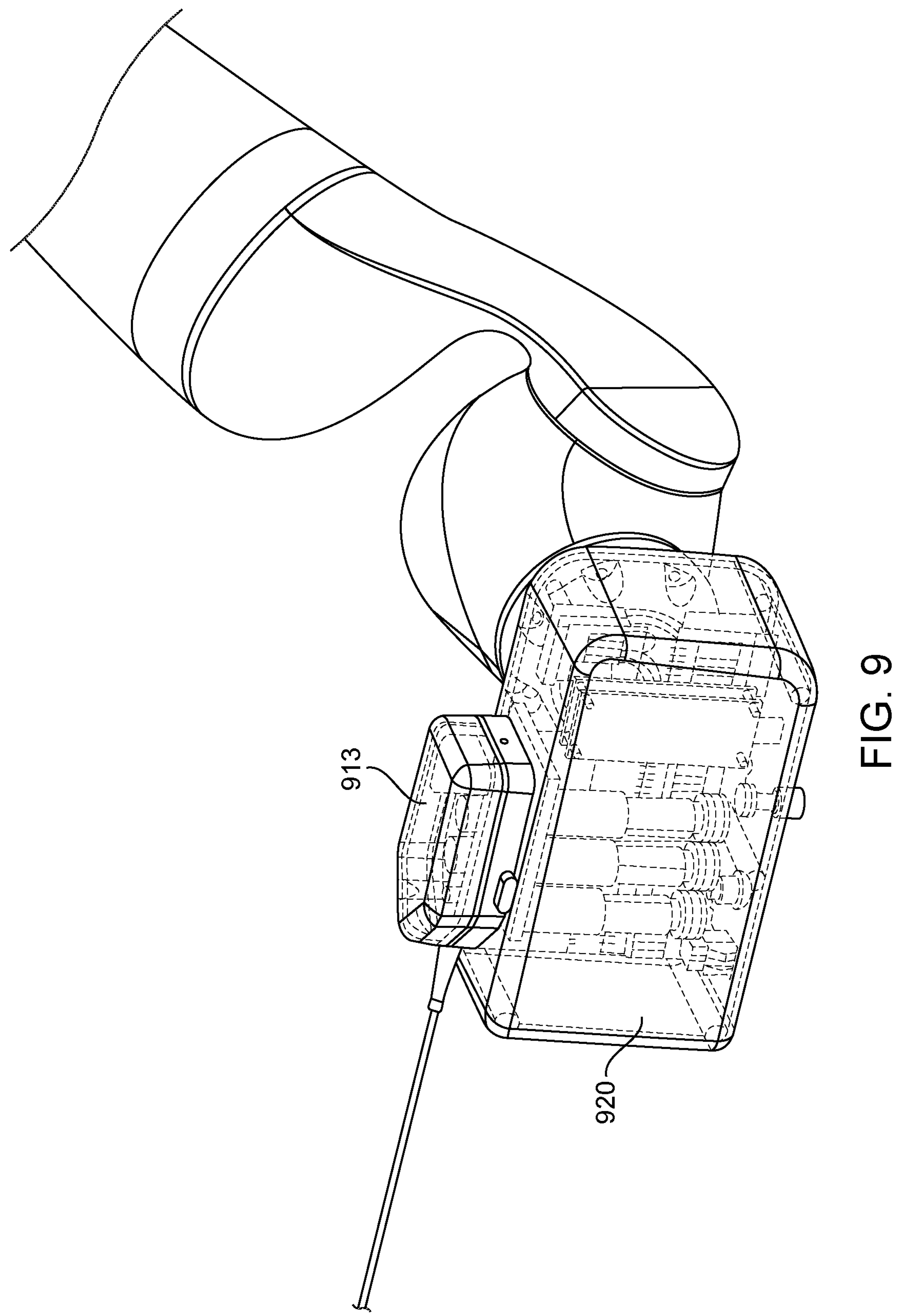
FIG. 9 shows an example of an instrument driving mechanism providing mechanical interface to a handle portion of a robotic bronchoscope, in accordance with some embodiments of the invention.
Figure 10:
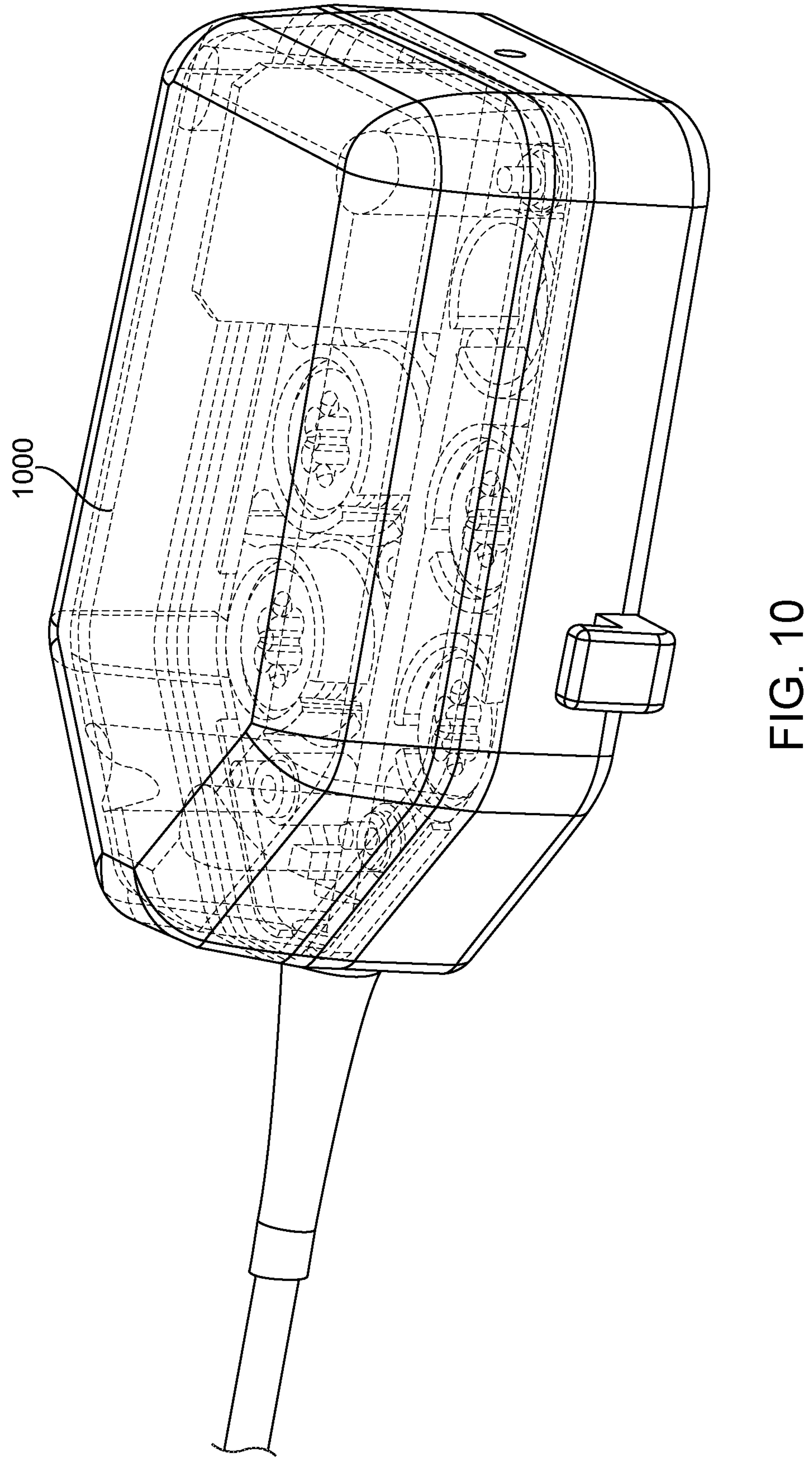
FIG. 10 shows an example handle portion of the robotic bronchoscope, in accordance with some embodiments of the invention.

FIGS. 8-10 show examples of a robotic bronchoscope, in accordance with some embodiments of the invention. As shown in FIG. 8, a robotic bronchoscope 820 may comprise a handle portion 813 and a flexible elongate member 811. In some embodiments, the flexible elongate member 811 may comprise a shaft, steerable tip and a steerable section. The robotic bronchoscope 820 can be the same as the steerable catheter assembly as described in FIG. 1. The robotic bronchoscope may be a single-use robotic endoscope. In some cases, only the catheter may be disposable. In some cases, at least a portion of the catheter may be disposable. In some cases, the entire robotic bronchoscope may be released from the instrument driving mechanism and can be disposed of The bronchoscope may contain varying levels of stiffness along its shaft, as to improve functional operation.

The robotic bronchoscope can be releasably coupled to an instrument driving mechanism 820. The instrument driving mechanism 820 may be mounted to the arm of the robotic support system or to any actuated support system as described elsewhere herein. The instrument driving mechanism may provide mechanical and electrical interface to the robotic bronchoscope 820. The mechanical interface may allow the robotic bronchoscope 820 to be releasably coupled to the instrument driving mechanism. For instance, the handle portion of the robotic bronchoscope can be attached to the instrument driving mechanism via quick install/release means, such as magnets and spring-loaded levels. In some cases, the robotic bronchoscope may be coupled or released from the instrument driving mechanism manually without using a tool.

FIG. 9 shows an example of an instrument driving mechanism 920 providing mechanical interface to the handle portion 913 of the robotic bronchoscope. As shown in the example, the instrument driving mechanism 920 may comprise a set of motors that are actuated to rotationally drive a set of pull wires of the catheter. The handle portion 913 of the catheter assembly may be mounted onto the instrument drive mechanism so that its pulley assemblies are driven by the set of motors. The number of pulleys may vary based on the pull wire configurations. In some cases, one, two, three, four, or more pull wires may be utilized for articulating the catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

FIG. 10 shows an example handle portion 1000 of the robotic bronchoscope, in accordance with some embodiments of the invention. In some case, the handle portion 1000 may be housing or comprise components configured to process image data, provide power, or establish communication with other external devices. In some cases, the communication may be wireless communication. For example, the wireless communications may include Wi-Fi, radio communications, Bluetooth, IR communications, or other types of direct communications. Such wireless communication capability may allow the robotic bronchoscope function in a plug-and-play fashion and can be conveniently disposed after single use. In some cases, the handle portion may comprise circuitry elements such as power sources for powering the electronics (e.g. camera and LED light source) disposed within the robotic bronchoscope or catheter.

The handle portion may be designed in conjunction with the catheter such that cables or fibers can be eliminated. For instance, the catheter portion may employ a design having a single working channel allowing instruments to pass through the robotic bronchoscope, as well as low cost electronics such as a chip-on-tip camera, illumination sources such as light emitting diode (LED) and EM sensors located at optimal locations in accordance with the mechanical structure of the catheter. This may allow for a simplified design of the handle portion. For instance, by using LEDs for illumination, the termination at the handle portion can be based on electrical soldering or wire crimping alone. For example, the handle portion may include a proximal board where the camera cable, LED cable, and EM sensor cable terminate while the proximal board connects to the interface of the handle portion and establishes the electrical connections to the instrument driving mechanism. As described above, the instrument driving mechanism is attached to the robot arm (robotic support system) and provides a mechanical and electrical interface to the handle portion. This may advantageously improve the assembly and implementation efficiency as well as simplify the manufacturing process and cost. In some cases, the handle portion along with the catheter may be disposed of after a single use.

Single-Use Steerable Catheter

Figure 11:
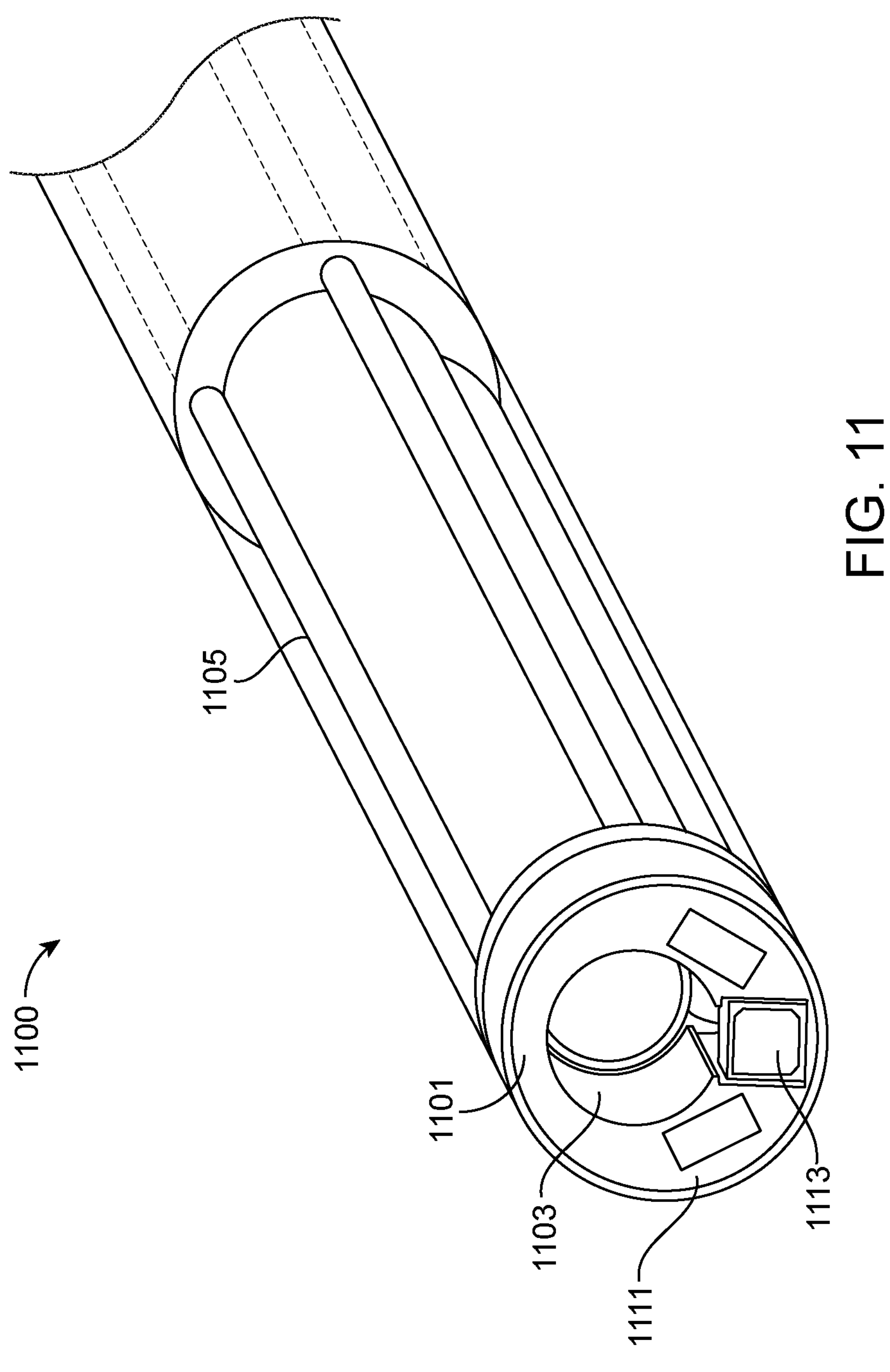
FIG. 11 shows an example steerable catheter, in accordance with some embodiments of the invention.

FIG. 11 shows an example steerable catheter 1100, in accordance with some embodiments of the invention. In some embodiments, the catheter may have a substantially integral design that one or more components may be integral to the catheter thereby simplifying the assembly, manufacturing process while preserving the kinematic, dynamic performance of the steerable catheter. As shown in the example, the steerable catheter may comprise an elongate member 1101 or a probing portion that is brought into proximity to the tissue and/or area that is to be examined. The elongate member 1101 may, in some cases, also be referred to as catheter. The catheter 1101 may comprise internal structures such as a working channel 1103 allowing tools as described elsewhere herein to be inserted through. In some cases, the working channel may have a dimension such as diameter of around 2 mm to be compatible with standard tools.

The catheter 1101 may be composed of suitable materials for desired flexibility or bending stiffness. In some cases, the materials of the catheter may be selected such that it may maintain structural support to the internal structures (e.g., working channel) as well as being substantially flexible (e.g., able to bend in various directions and orientations). For example, the catheter can be made of any suitable material such as Provista Copolymer, vinyl (such as polyvinyl chloride), Nylon (such as vestamid, grilamid), pellethane, polyethylene, polypropylene, polycarbonate, polyester, silicon elastomer, acetate and so forth. In some cases, the materials may be polymer material, biocompatible polymer material and the catheter may be sufficiently flexible to be advancing through a path with a small curvature without causing pain to a subject. In some cases, the catheter may comprise a sheath. The sheath may not be the same length of the catheter. The sheath may be shorter than the catheter to provide desired support. Alternatively, the catheter may be substantially a single-piece component.

In some cases, the distal portion or tip of the catheter may be substantially flexible such that it can be steered into one or more directions (e.g., pitch, yaw). The catheter may comprise a tip portion, bending section, and insertion shaft same as those as described in FIGS. 1-5. In some embodiments, the catheter may have variable bending stiffness along the longitudinal axis direction. For instance, the catheter may comprise multiple segments having different bending stiffness (e.g., flexible, semi-rigid, and rigid). The bending stiffness may be varied by selecting materials with different stiffness/rigidity, varying structures in different segments (e.g., cuts, patterns), adding additional supporting components or any combination of the above. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires 1105. The distal portion of the catheter may be made of any suitable material such as co-polymers, polymers, metals or alloys such that it can be bent by the pull wires. In some embodiments, the proximal end or portion of one or more pull wires 1105 may be operatively coupled to various mechanisms (e.g., gears, pulleys, etc.) in the handle portion of the catheter assembly. The pull wire 1105 may be a metallic wire, cable or thread, or it may be a polymeric wire, cable or thread. The pull wire 1105 can also be made of natural or organic materials or fibers. The pull wire 1105 can be any type of suitable wire, cable or thread capable of supporting various kinds of loads without deformation, significant deformation, or breakage. The distal end or portion of one or more pull wires 1105 may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

As described above, the pull wires may be made of any suitable material such as stainless steel (e.g. SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals. Pull wires may run through the lumen of one or more load transmission tubes as described elsewhere herein.

The catheter may have a dimension so that one or more electronic components can be integrated to the catheter. For example, the outer diameter of the distal tip may be around 4 to 4.4 millimeters (mm), and the diameter of the working channel may be around 2 mm such that one or more electronic components can be embedded into the wall of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera 1113. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources 1111 positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

Figure 12:
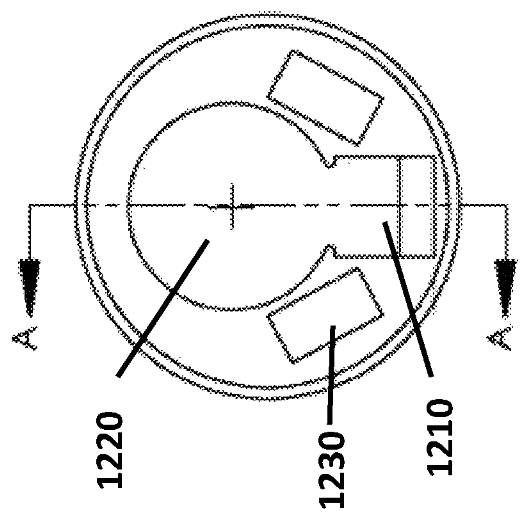
FIG. 12 shows an example distal portion of a catheter with integrated imaging device and illumination device.
Figure 12:
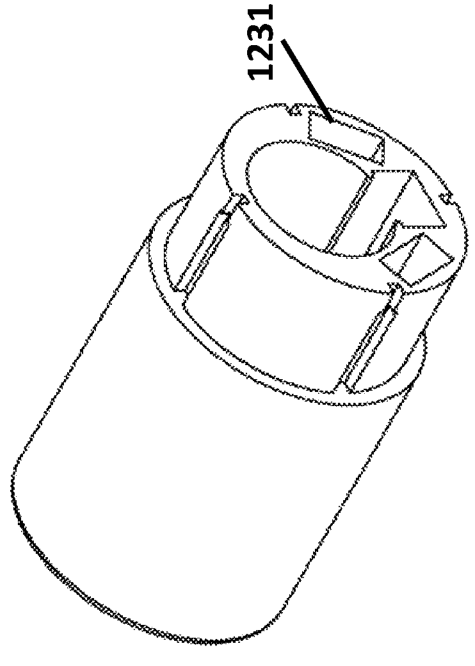

The imaging device and the illumination device may be integrated to the catheter. For example, the distal portion of the catheter may comprise suitable structures matching at least a dimension of the imaging device and the illumination device. The imaging device and the illumination device may be embedded into the catheter. FIG. 12 shows an example distal portion of the catheter with integrated imaging device and the illumination device. A camera may be located at the distal portion. The distal tip may have a structure to receive the camera, illumination device and/or the location sensor. For example, the camera may be embedded into a cavity 1210 at the distal tip of the catheter. The cavity 1210 may be integrally formed with the distal portion of the cavity and may have a dimension matching a length/width of the camera such that the camera may not move relative to the catheter. The camera may be adjacent to the working channel 1220 of the catheter to provide near field view of the tissue or the organs. In some cases, the attitude or orientation of the imaging device may be controlled by controlling a rotational movement (e.g., roll) of the catheter.

The power to the camera may be provided by a wired cable. In some cases, the cable wire may be in a wire bundle providing power to the camera as well as illumination elements or other circuitry at the distal tip of the catheter. The camera and/or light source may be supplied with power from a power source located at the handle portion via wires, copper wires, or via any other suitable means running through the length of the catheter. In some cases, real-time images or video of the tissue or organ may be transmitted to an external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the catheter to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

In conventional endoscopy, illumination light may be provided by fiber cables that transfer the light of a light source located at the proximal end of the endoscope, to the distal end of the robotic endoscope. In some embodiments of the disclosure, miniaturized LED lights may be employed and embedded into the distal portion of the catheter to reduce the design complexity. In some cases, the distal portion may comprise a structure 1230 having a dimension matching a dimension of the miniaturized LED light source. As shown in the illustrated example, two cavities 1230 may be integrally formed with the catheter to receive two LED light sources. For instance, the outer diameter of the distal tip may be around 4 to 4.4 millimeters (mm) and diameter of the working channel of the catheter may be around 2 mm such that two LED light sources may be embedded at the distal end. The outer diameter can be in any range smaller than 4 mm or greater than 4.4 mm, and the diameter of the working channel can be in any range according to the tool's dimensional or specific application. Any number of light sources may be included. The internal structure of the distal portion may be designed to fit any number of light sources.

In some cases, each of the LEDs may be connected to power wires which may run to the proximal handle. In some embodiment, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover 1231 may be placed at the forwarding end face of the distal tip providing precise positioning of the LEDs as well as sufficient room for the glue. The cover 1231 may be composed of transparent material matching the refractive index of the glue so that the illumination light may not be obstructed.

In some embodiments, one or more sensors may be embedded into the distal portion of the catheter. In conventional robotic bronchoscopes, sensors may be used to track the tip position which are usually located at the distal tip thereby causing an increased size of the tip. The provided steerable catheter may bundle one or more electronic components to provide a compact design. In some cases, the illumination light source and one or more position sensors may be combined into a bundle. FIG. 13 shows an example of a compact configuration of the electronic elements located at the distal portion. In some embodiments, position sensors such as electromagnetic (EM) sensors may be used to accurately track the position of the distal tip of the catheter. For example, electromagnetic coils 1310 located on the distal end may be used with the electromagnetic tracking system to detect the position and orientation of the distal tip of the catheter while it is disposed within an anatomical system (e.g., anatomical luminal network). In some cases, the coils may be angled to provide sensitivity to electromagnetic fields along different axes, giving the disclosed navigational systems the ability to measure a six-degrees of freedom: three positional and three angular.

In some cases, one or more EM sensors 1310 may be located at the distal portion and may be placed adjacent to or behind the illumination light sources 1320 (e.g., LEDs) in a stereoscopic arrangement. In some cases, an EM sensor and a LED light source may form a bundle 1300. The power cables of the EM sensors may be bundled together with the wires of the LEDs to provide reduced space and complexity. In some cases, the stereoscopic alignment may provide differential 5D measurement, or a fused 6D measurement, that allows accurate positioning and orientation-sensing of the catheter distal tip. During the procedure, the EM field generator positioned next to, under, or above, a patient torso may locate the EM sensors thereby tracking the location of the catheter tip in real-time.

Pull Wire Configurations and Design

Figure 14:
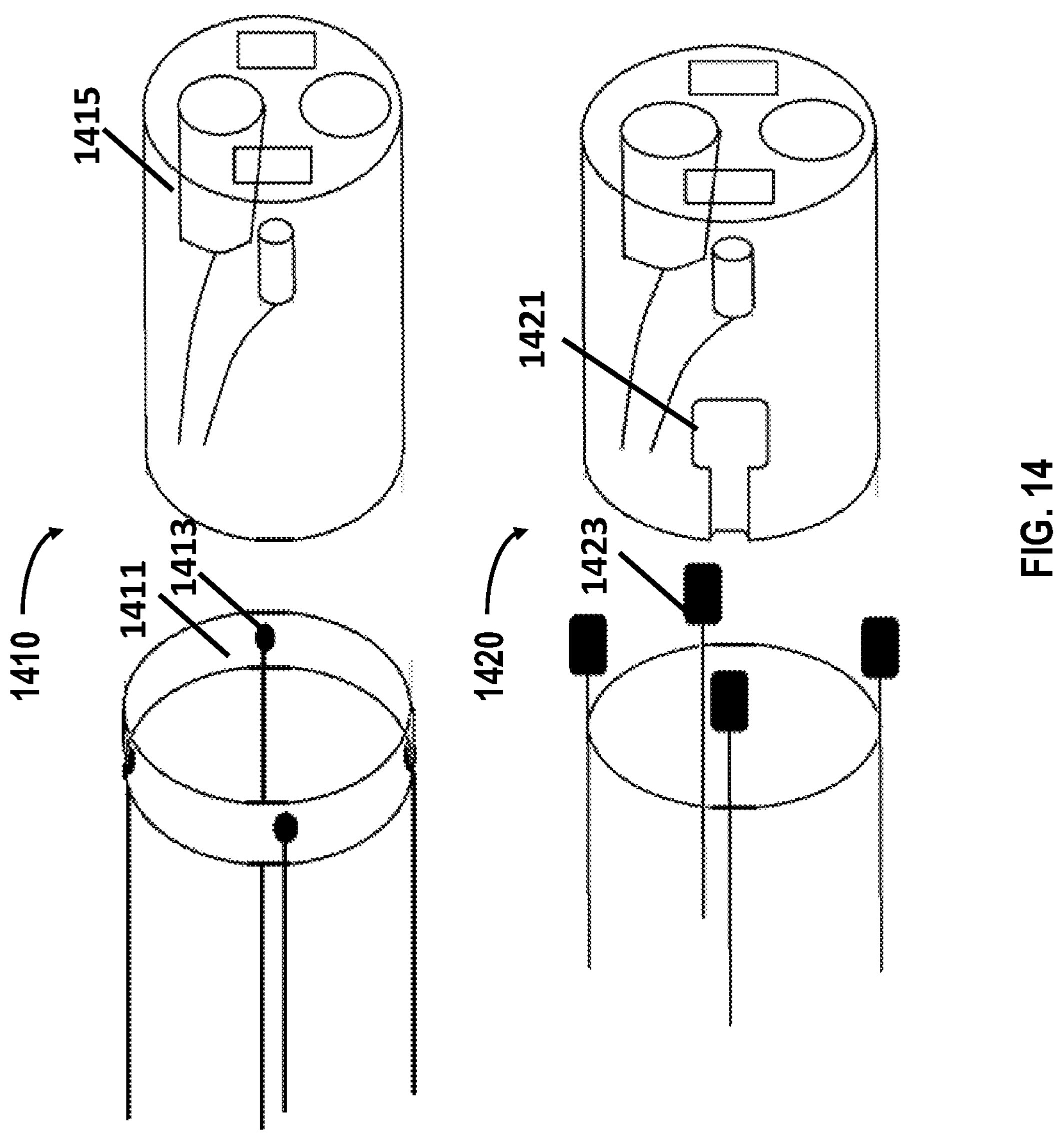
FIG. 14 shows an example of a conventional configuration of pull wires attached to a control ring structure and a novel configuration of the present disclosure.

The robotic bronchoscope may comprise one or more pull wires for controlling articulation of the catheter. In conventional endoscopes, the distal end or portion of the one or more pull wires may be anchored or mounted to a control ring, such that operation of the pull wires by the control unit may apply force or tension to the control ring which may steer or articulate (e.g., up, down, pitch, yaw, or any direction in-between) certain section or portion (e.g., distal section) of the catheter. FIG. 14 shows an example of a conventional configuration of pull wires 1413 attached to a control ring structure 1411 and a novel configuration 1420 of the present disclosure. The control ring may be attached to the distal end of the catheter 1415. Usually the tip of the pull wires is welded or soldered to the control ring 1411 and the control ring may also be attached to the distal tip by welding. The welding process can be costly, cumbersome and complex. Moreover, when one pull wire is broken or malfunctions, the entire steering control functionality may be affected.

The provided robotic bronchoscope may comprise individually controlled pull wires each of which is connected to the distal portion directly. As shown in the example 1420, the one or more pull wires 1423 may be attached to an integrally formed structure 1421 of the distal portion. For example, the integrally formed structure 1421 may be grooves that are molded with the distal tip. The grooves may have a dimension or size that match the dimension of the distal end 1421 of the pull wire such that the pull wire can be conveniently crimped at distal end. This may advantageously improve the assembly efficiency. In some instances, the pull wires may be rigidly affixed to the grooves at the distal end such that the distal end of the pull wire may not be permitted to move relative to the distal portion of the catheter.

The pull wire configuration may also provide improved reliability in steering the distal portion. For instance, as each pull wire is individually connected to the distal portion and individually controlled, the articulation force may be dynamically adjusted according to different pull wire configurations. For instance, the articulation force may be recalculated and the control signals for controlling the pull wires may be dynamically adjusted based on the available pull wires in case a pull wire is broken.

Figure 15:
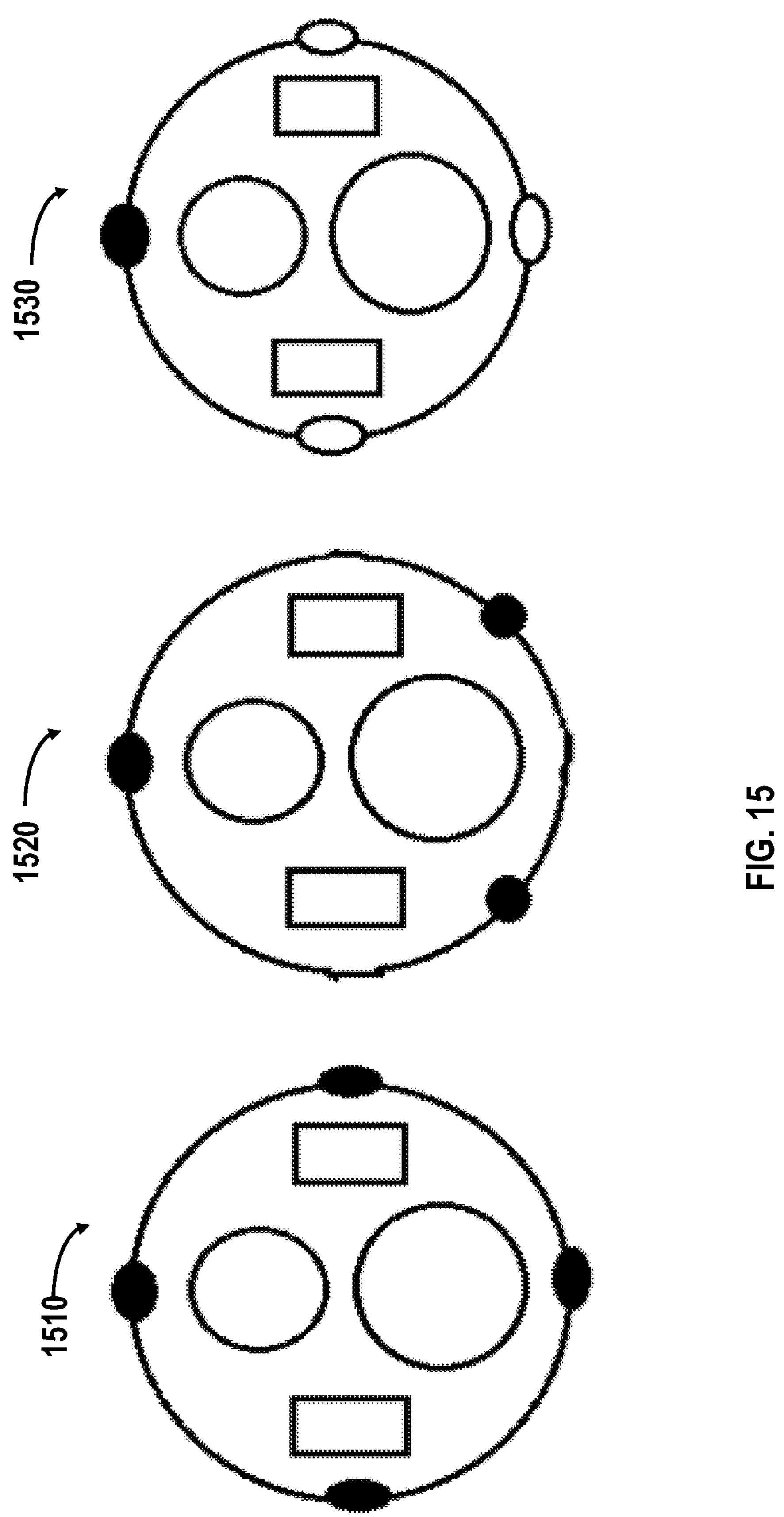
FIG. 15 shows various configurations of pull wires for a robotic catheter system, in accordance with some embodiments of the invention.

The convenient assembly of pull wires to the distal portion may also allow for flexibility in designing pull wire configurations. For example, the number or combination of pull wires can be selected or adjusted dynamically to meet different performance or design requirements. FIG. 15 shows various configurations of pull wires for a robotic catheter system. In some embodiments, the integral structure (grooves) for receiving the pull wires may be pre-fabricated. For example, four grooves may be integrally formed with the catheter and one or more pull wires may be fixedly connected/crimped to one or more grooves selected from the plurality of grooves to form different configurations 1510, 1530. As shown in the example, any number of grooves/slots or any given subset of grooves/slots can be selected to receive or couple to the pull wires at one end. In some cases, once a combination of slots/grooves is selected to be coupled to the corresponding pull wires, a pull-wire configuration pattern may be formed and a mapping relationship between the selected grooves/slots and the pull wires may be transmitted to the control unit. Control signals may then be generated during articulation based on the mapping relationship to achieve desired articulation force.

In another example, the pre-fabricated grooves may have various configurations. For instance, a three-pull-wire configuration 1520 may have three grooves separated by about 120°. In some cases, a virtual mapping algorithm may map the three-wire configuration to a four-wire configuration. The virtual mapping algorithm can also be utilized to update a new mapping relationship when one or more pull wires are malfunctioning/broken during operation. Such integral design of the pull wire configurations advantageously simplifies the assembly, manufacturing process while preserving the kinematic, dynamic performance of the catheter.

Guidewire with an Inflatable Tip

In some embodiments, a guidewire may be used during bronchoscopy operation. A guidewire may usually be inserted far beyond the tip of the bronchoscope to enter the desired air passageway first, and subsequently allow the bronchoscope to slide over the guidewire into the selected passage. Due to the guidewire's smaller diameter in comparison to that of a bronchoscope, the guidewire may not have sufficient stiffness and/or enough frictional force to anchor the guidewire within the air passages.

Figure 16:
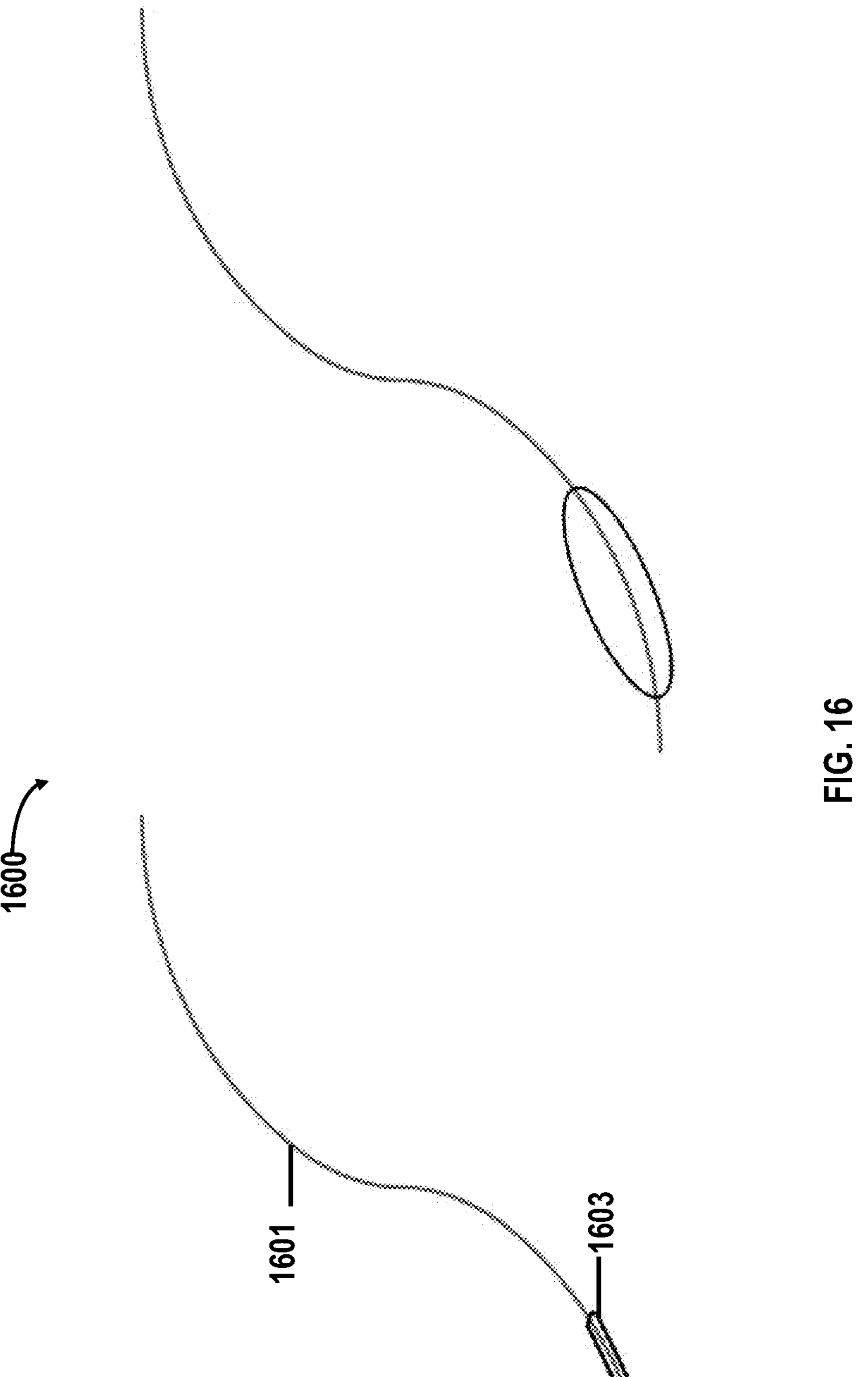
FIG. 16 shows an example of a guidewire with inflatable tip, in accordance with some embodiments of the invention.

The guidewire of the present disclosure may have an expandable outside diameter feature at the tip. FIG. 16 shows an example of a guidewire 1600 with inflatable tips. The guidewire 1601 may be inserted through the working channel of the catheter/bronchoscope to assist in navigation of the air passages in the lung. In some cases, the guidewire may be extended past the tip of the catheter into the desired airway and the catheter may then slide over the guidewire to reach the desired location. The inflatable tip can be implemented using various suitable methods. For example, an additional component 1603 such as an inflatable balloon may be positioned at or close to the distal end of the guidewire. The balloon may be connected through the working channel to a balloon inflation source or pump for inflation or deflation of the balloon.

In some cases, the guidewire may comprise perforated holes. The diameter of the deflated balloon may be equal to the diameter of the elongate arm (e.g. bronchoscope catheter). In some cases, the diameter of the deflated balloon may be slightly greater than the elongate arm. The guidewire may be able to move distally or proximally. The guidewire may be attached to an air pump to inject and withdraw the air from the guidewire, which consequently inflates and deflates the balloon respectively. During the insertion of guidewire into the airway, the balloon may remain deflated. while the proper location is reached, the balloon will be inflated by pumping in the air. Once the bronchoscope reaches the desired forward position, the balloon may be deflated by pumping the air out that may allow the guidewire to move forward. In some embodiments, the inflatable tip can be made of collapsible mesh structures using materials, such as shape memory alloy (SMA), electro-active polymer (EAP), and ferromagnetic fluids, with its corresponding inflation and deflation control mechanisms. The anchoring element can have any other form to secure the anchoring of the guidewire. For example, the anchoring element may be metal wires that can expand or collapse radially. The anchoring element may be actuated by a slide actuator that is slid linearly to cause the anchoring element to change its position and in particular, to cause the anchoring element to either deploy or to be placed back into a collapsed position. The sliding action of the actuator may be translated into a change in the position (condition) of the anchoring element (e.g., anchoring element deploys and radially expands so as to provide a structure that anchors the guidewire in place, or conversely, anchoring element radially contracts and is returned to a collapsed state.

Figure 17:
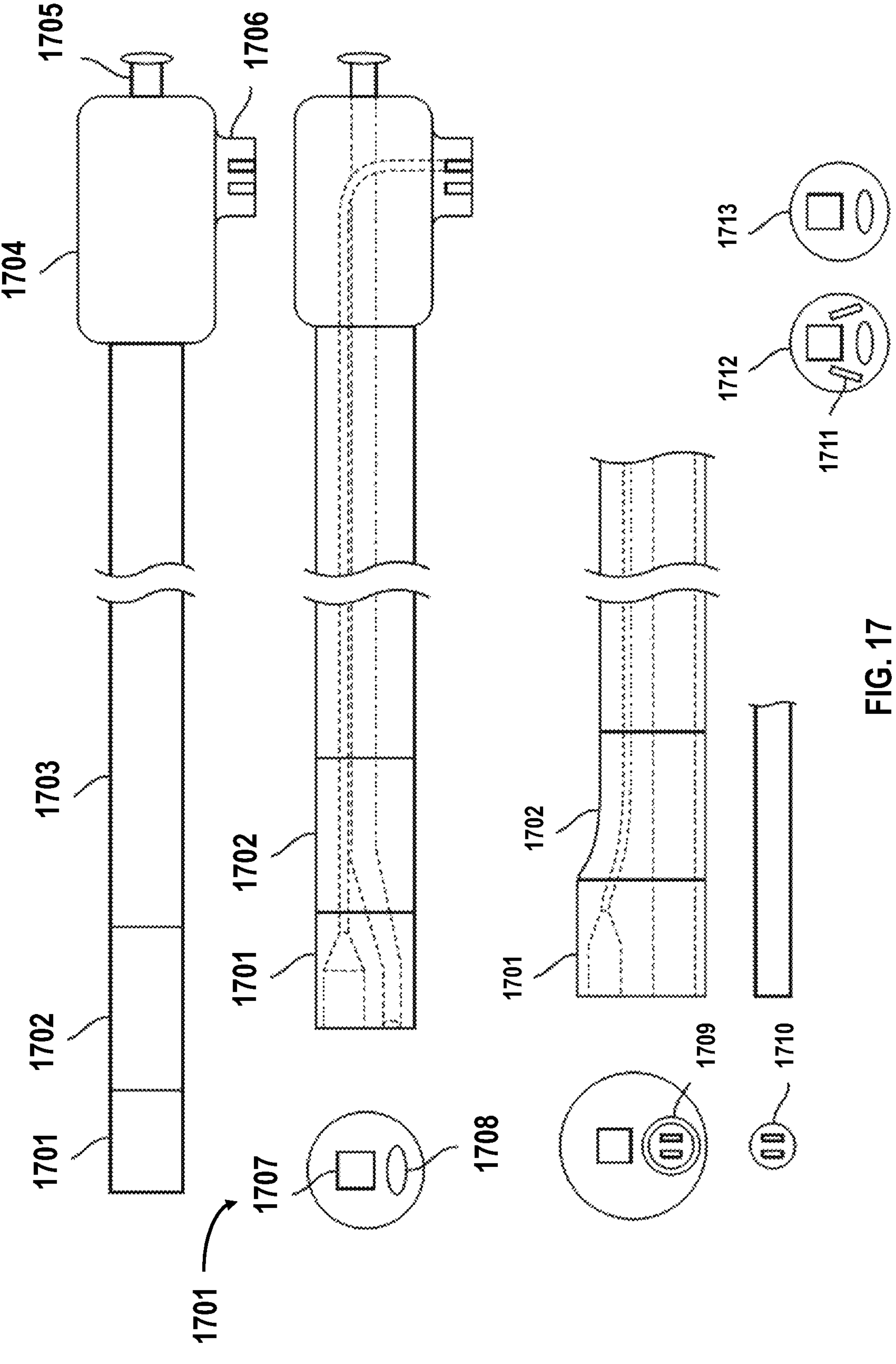
FIG. 17 shows an example of endoscope tip design.

FIG. 17 shows another example of a catheter tip design 1701. In the illustrated example, the tip 1701 may have a diameter greater than that of the bending section 1702 and/or the shaft 1703. The working channel 1708 may be deformable (e.g., expandable/squeezable). The working channel 1708 may be formed of elastic material (e.g., plastic) that can accommodate instruments with variable dimensions. For example, larger instruments such as biopsy, therapeutic instrument, energy device may expand the tip portion of the working channel when being inserted through the working channel 1708.

In a first example 1710, LED light source or light guide can be swapped out after the endoscope reaches the target location. In a second example 1712 the LED light source 1711 may be embedded into the tip. In a third example 1713, the LED light source may be embedded in the tip while the light guide may be removable. The tip may comprise other electronic components such as camera 1707 as described elsewhere herein. The endoscope may also comprise a handle portion 1704 that is similar to the handle as described elsewhere herein. For example, the handle portion may comprise lures 1705 and electric interface 1706 for various functionalities.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An articulating flexible endoscope comprising:

a distal tip portion that is steerable via a driving mechanism;

a bending section connected to the distal tip portion at a distal end of the bending section, and connected to a shaft portion at a transition interface which comprises a ring structure, wherein the bending section is articulated by a plurality of pull wires; and the shaft portion comprising a wall forming a central tubular bore housing a plurality of load transmission tubes for accommodating the plurality of pull wires, wherein a distal end of the plurality of load transmission tubes is anchored to the ring structure of the transition interface thereby forming a modular component for easy assembly to the bending section and the shaft portion, wherein a proximal end of the plurality of transmission tubes is fixed to a proximal end of the shaft portion such that only the distal end and proximal end of the plurality of load transmission tubes are connected to the shaft portion thereby transmitting load directly from the distal end to the proximal end without compressing the wall of the shaft portion, and wherein a length of each load transmission tube is greater than a length of the shaft portion between the transition interface and the proximal end of the shaft portion by a predetermined percentage, and wherein the predetermined percentage allows for a movement of each load transmission tube within the central tubular bore of the shaft portion to adapt to geometry changes to the length of the shaft portion.

2. The articulating flexible endoscope of claim 1, wherein the distal tip portion comprises a structure to integrate an imaging device, a position sensor, and an illumination device.

3. The articulating flexible endoscope of claim 1, wherein each of the plurality of pull wires is placed inside of a lumen of a respective load transmission tube from the plurality of load transmission tubes.

4. The articulating flexible endoscope of claim 1, wherein the bending section is bent by the plurality of pull wires in two or more directions.

5. The articulating flexible endoscope of claim 1, wherein the shaft portion includes a tube with an integrally formed structure to vary a stiffness of the shaft portion.

6. The articulating flexible endoscope of claim 1, further comprising a deformable working channel.

7. The articulating flexible endoscope of claim 1, further comprising a handle portion, wherein the handle portion includes one or more components configured to process image data, provide power to one or more electronic components located at the distal tip portion, or establish communication with an external device.

8. The articulating flexible endoscope of claim 7, wherein the handle portion comprises an interface configured to couple the handle portion to an instrument driving mechanism, and wherein the interface comprises an electrical interface and a mechanical interface.

9. The articulating flexible endoscope of claim 1, wherein the predetermined percentage is determined to ensure that the length of a particular load transmission tube is greater than the length of the shaft portion when the particular load transmission tube is under axial compression.

10. The articulating flexible endoscope of claim 1, wherein the distal end of the plurality of load transmission tubes is anchored to the ring structure of the transition interface to reduce an abrupt stiffness change between the shaft portion and the bending section.

11. A disposable endoscope comprising:

a distal tip portion including an imaging device, a position sensor and an illumination device;

a bending section connected to the distal tip portion at a distal end of the bending section, and connected to a shaft portion at a proximal end of the bending section, wherein the bending section is articulated by a plurality of pull wires; and the shaft portion comprising a wall forming a central tubular bore housing a plurality of load transmission tubes for accommodating the plurality of pull wires, wherein a distal end of the plurality of load transmission tubes is anchored to a junction interface between the bending section and the shaft portion thereby forming a modular component for easy assembly to the bending section and the central tubular bore, wherein a proximal end of the plurality of transmission tubes is fixed to a proximal end of the shaft portion such that only the distal end and proximal end of the plurality of load transmission tubes are connected to the shaft portion thereby transmitting load directly from the distal end to the proximal end without compressing the wall of the shaft portion, and wherein a length of each load transmission tube is greater than a length of the shaft portion between the junction interface and the proximal end of the shaft portion by a predetermined percentage to reduce an axial compression force applied to the shaft portion thereby improving stability of the shaft portion, and wherein the predetermined percentage allows for a movement of each load transmission tube within the central tubular bore of the shaft portion to adapt to geometry changes to the length of the shaft portion.

12. The disposable endoscope of claim 11, wherein the distal tip portion comprises a structure to receive the imaging device, the position sensor, and the illumination device.

13. The disposable endoscope of claim 11, wherein the imaging device, the position sensor, and the illumination device are arranged into a compact configuration.

14. The disposable endoscope of claim 11, wherein each of the plurality of pull wires is placed inside of a lumen of a respective load transmission tube from the plurality of load transmission tubes.

15. The disposable endoscope of claim 11, wherein the plurality of pull wires are movable relative to the plurality of load transmission tubes.

16. The disposable endoscope of claim 11, wherein the bending section is bent by the plurality of pull wires in two or more directions.

17. The disposable endoscope of claim 11, wherein the predetermined percentage is determined to ensure that the length of a particular load transmission tube is greater than the length of the shaft portion when the particular load transmission tube is under axial compression.

18. The disposable endoscope of claim 11, wherein the distal end of the plurality of load transmission tubes is anchored to the junction interface via a cutout feature on the shaft portion.

* * * * *